US008486132B2

(12) United States Patent
Snow et al.

(10) Patent No.: US 8,486,132 B2
(45) Date of Patent: Jul. 16, 2013

(54) DEVICES AND METHODS FOR CONTROLLING EXPANDABLE PROSTHESES DURING DEPLOYMENT

(75) Inventors: David W. Snow, San Carlos, CA (US); Denise Demarais, Los Gatos, CA (US); Stuart Lin, Mountain View, CA (US)

(73) Assignee: J.W. Medical Systems Ltd., Weihai Shandong (CN)

( * ) Notice: Subject to any disclaimer, the term of this patent is extended or adjusted under 35 U.S.C. 154(b) by 955 days.

(21) Appl. No.: 11/689,927

(22) Filed: Mar. 22, 2007

(65) Prior Publication Data
US 2008/0234795 A1      Sep. 25, 2008

(51) Int. Cl.
    *A61F 2/06* (2006.01)
(52) U.S. Cl.
    USPC ....... 623/1.16; 623/1.11; 623/1.12; 623/1.15; 623/1.23
(58) Field of Classification Search
    USPC .................................. 623/6.12, 6.16
    See application file for complete search history.

(56) References Cited

U.S. PATENT DOCUMENTS

| | | |
|---|---|---|
| 4,069,825 A | 1/1978 | Akiyama |
| 4,564,014 A | 1/1986 | Fogarty et al. |
| 4,580,568 A | 4/1986 | Gianturco |
| 4,681,110 A | 7/1987 | Wiktor |
| 4,690,684 A | 9/1987 | McGreevy et al. |
| 4,733,665 A | 3/1988 | Palmaz |
| 4,739,762 A | 4/1988 | Palmaz |
| 4,748,982 A | 6/1988 | Horzewski et al. |
| 4,762,129 A | 8/1988 | Bonzel |
| 4,770,176 A | 9/1988 | McGreevy et al. |
| 4,775,337 A | 10/1988 | Van Wagener et al. |
| 4,776,337 A | 10/1988 | Palmaz |
| 4,886,062 A | 12/1989 | Wiktor |

(Continued)

FOREIGN PATENT DOCUMENTS

| | | |
|---|---|---|
| DE | 1 953 1659 | 3/1997 |
| DE | 1 963 0469 | 1/1998 |

(Continued)

OTHER PUBLICATIONS

International Search Report and Written Opinion of PCT Application No. PCT/US08/57202 , dated Oct. 23, 2008, 11 pages total.

(Continued)

*Primary Examiner* — Gary Jackson
*Assistant Examiner* — Kevin Everage
(74) *Attorney, Agent, or Firm* — Kilpatrick Townsend & Stockton LLP

(57) ABSTRACT

A catheter for delivering a prosthesis to a treatment site in a body lumen comprises an elongate flexible member and a sheath slidably disposed thereover. A plurality of self-expanding tubular prostheses are carried in axially spaced apart locations along the elongate member, within the sheath. The prostheses may be selectively interlocked with one another and are constrained by the sheath in a radially contracted configuration. The prostheses are separately releasable from the sheath when the sheath is retracted relative to the elongate member. The catheter also has a pusher member slidably disposed along the elongate member within the sheath. The pusher is adapted to move past the prostheses in a first direction without displacing the prostheses, while in a second direction the pusher engages a selected prosthesis so as to move the prosthesis with the pusher to interlock the selected prosthesis with a second prosthesis.

26 Claims, 10 Drawing Sheets

U.S. PATENT DOCUMENTS

| | | | |
|---|---|---|---|
| 4,891,225 A | 1/1990 | Langer et al. |
| 4,950,227 A | 8/1990 | Savin et al. |
| 4,988,356 A | 1/1991 | Crittenden et al. |
| 4,994,066 A | 2/1991 | Voss |
| 4,994,069 A | 2/1991 | Ritchart et al. |
| 4,994,298 A | 2/1991 | Yasuda |
| 5,013,318 A | 5/1991 | Spranza, III |
| 5,035,706 A | 7/1991 | Gianturco et al. |
| 5,040,548 A | 8/1991 | Yock |
| 5,061,273 A | 10/1991 | Yock |
| 5,064,435 A | 11/1991 | Porter |
| 5,092,877 A | 3/1992 | Pinchuk |
| 5,102,417 A | 4/1992 | Palmaz |
| 5,104,404 A | 4/1992 | Wolff |
| 5,122,154 A | 6/1992 | Rhodes |
| 5,135,535 A | 8/1992 | Kramer |
| 5,158,548 A | 10/1992 | Lau et al. |
| 5,192,297 A | 3/1993 | Hull |
| 5,195,984 A | 3/1993 | Schatz |
| 5,201,757 A | 4/1993 | Heyn et al. |
| 5,217,495 A | 6/1993 | Kaplan et al. |
| 5,219,355 A | 6/1993 | Parodi et al. |
| 5,226,913 A | 7/1993 | Pinchuk |
| 5,246,421 A | 9/1993 | Saab |
| 5,273,536 A | 12/1993 | Savas |
| 5,282,824 A | 2/1994 | Gianturco |
| 5,300,085 A | 4/1994 | Yock |
| 5,312,415 A | 5/1994 | Palermo |
| 5,328,469 A | 7/1994 | Coletti |
| 5,334,187 A | 8/1994 | Fischell et al. |
| 5,391,172 A | 2/1995 | Williams et al. |
| 5,421,955 A | 6/1995 | Lau et al. |
| 5,443,498 A | 8/1995 | Fontaine |
| 5,445,646 A | 8/1995 | Euteneuer et al. |
| 5,456,713 A | 10/1995 | Chuter |
| 5,458,615 A | 10/1995 | Klemm et al. |
| 5,470,315 A | 11/1995 | Adams |
| 5,478,349 A | 12/1995 | Nicholas |
| 5,484,444 A | 1/1996 | Braunschweiler et al. |
| 5,490,837 A | 2/1996 | Blaeser et al. |
| 5,496,346 A | 3/1996 | Horzewski et al. |
| 5,501,227 A | 3/1996 | Yock |
| 5,507,768 A | 4/1996 | Lau et al. |
| 5,507,771 A | 4/1996 | Gianturco |
| 5,514,093 A | 5/1996 | Ellis et al. |
| 5,514,154 A | 5/1996 | Lau et al. |
| 5,522,882 A | 6/1996 | Gaterud et al. |
| 5,527,354 A | 6/1996 | Fontaine et al. |
| 5,533,968 A | 7/1996 | Muni et al. |
| 5,534,007 A | 7/1996 | St. Germain et al. |
| 5,545,209 A | 8/1996 | Roberts et al. |
| 5,549,551 A | 8/1996 | Peacock, III et al. |
| 5,549,563 A | 8/1996 | Kronner |
| 5,549,635 A | 8/1996 | Solar |
| 5,554,181 A | 9/1996 | Das |
| 5,562,725 A | 10/1996 | Schmitt et al. |
| 5,571,086 A | 11/1996 | Kaplan et al. |
| 5,591,195 A | 1/1997 | Taheri et al. |
| 5,593,412 A | 1/1997 | Martinez et al. |
| 5,607,444 A | 3/1997 | Lam |
| 5,607,463 A | 3/1997 | Schwartz et al. |
| 5,628,755 A | 5/1997 | Heller et al. |
| 5,628,775 A | 5/1997 | Jackson et al. |
| 5,634,928 A | 6/1997 | Fischell et al. |
| 5,639,274 A | 6/1997 | Fischell et al. |
| 5,662,675 A | 9/1997 | Polanskyj Stockert et al. |
| 5,662,703 A | 9/1997 | Yurek et al. |
| 5,670,161 A | 9/1997 | Healy et al. |
| 5,676,654 A | 10/1997 | Ellis et al. |
| 5,683,451 A | 11/1997 | Lenker et al. |
| 5,690,644 A | 11/1997 | Yurek et al. |
| 5,693,085 A | 12/1997 | Buirge et al. |
| 5,697,948 A | 12/1997 | Marin et al. |
| 5,697,971 A | 12/1997 | Fischell et al. |
| 5,702,418 A | 12/1997 | Ravenscroft |
| 5,702,419 A | 12/1997 | Berry et al. |
| 5,709,701 A | 1/1998 | Parodi |
| 5,716,393 A | 2/1998 | Lindenberg et al. |
| 5,722,669 A | 3/1998 | Shimizu et al. |
| 5,723,003 A | 3/1998 | Winston et al. |
| 5,735,869 A | 4/1998 | Fernandez-Aceytuno |
| 5,749,848 A | 5/1998 | Jang et al. |
| 5,749,890 A | 5/1998 | Shaknovich |
| 5,749,921 A | 5/1998 | Lenker et al. |
| 5,755,772 A | 5/1998 | Evans et al. |
| 5,755,776 A | 5/1998 | Al-Saadon |
| 5,755,781 A | 5/1998 | Jayaraman |
| 5,769,882 A | 6/1998 | Fogarty et al. |
| 5,772,669 A | 6/1998 | Vrba |
| 5,776,141 A | 7/1998 | Klein et al. |
| 5,792,144 A | 8/1998 | Fischell et al. |
| 5,797,951 A | 8/1998 | Mueller et al. |
| 5,800,519 A | 9/1998 | Sandock |
| 5,807,398 A | 9/1998 | Shaknovich |
| 5,824,040 A | 10/1998 | Cox et al. |
| 5,824,041 A | 10/1998 | Lenker et al. |
| 5,833,694 A | 11/1998 | Poncet |
| 5,836,964 A | 11/1998 | Richter et al. |
| 5,843,092 A | 12/1998 | Heller et al. |
| 5,855,563 A | 1/1999 | Kaplan et al. |
| 5,858,556 A | 1/1999 | Eckert et al. |
| 5,870,381 A | 2/1999 | Kawasaki et al. |
| 5,879,370 A | 3/1999 | Fischell et al. |
| 5,891,190 A | 4/1999 | Boneau |
| 5,895,398 A | 4/1999 | Wensel et al. |
| 5,899,935 A | 5/1999 | Ding |
| 5,902,332 A | 5/1999 | Schatz |
| 5,919,175 A | 7/1999 | Sirhan |
| 5,921,971 A | 7/1999 | Agro et al. |
| 5,922,020 A | 7/1999 | Klein et al. |
| 5,941,869 A | 8/1999 | Patterson et al. |
| 5,951,585 A | 9/1999 | Cathcart et al. |
| 5,961,536 A | 10/1999 | Mickley et al. |
| 5,968,069 A | 10/1999 | Dusbabek et al. |
| 5,972,027 A | 10/1999 | Johnson |
| 5,976,107 A | 11/1999 | Mertens et al. |
| 5,976,155 A | 11/1999 | Foreman et al. |
| 5,980,484 A | 11/1999 | Ressemann et al. |
| 5,980,486 A | 11/1999 | Enger |
| 5,980,514 A | 11/1999 | Kupiecki et al. |
| 5,980,552 A | 11/1999 | Pinchasik et al. |
| 5,984,957 A | 11/1999 | Laptewicz, Jr. et al. |
| 5,989,280 A | 11/1999 | Euteneuer et al. |
| 5,993,484 A | 11/1999 | Shmulewitz |
| 5,997,563 A | 12/1999 | Kretzers et al. |
| 6,004,328 A | 12/1999 | Solar |
| 6,007,517 A | 12/1999 | Anderson |
| 6,010,530 A | 1/2000 | Goicoechea |
| 6,022,359 A | 2/2000 | Frantzen |
| 6,022,374 A | 2/2000 | Imran |
| 6,027,519 A | 2/2000 | Stanford |
| 6,033,434 A | 3/2000 | Borghi |
| 6,036,725 A | 3/2000 | Avellanet |
| 6,039,721 A | 3/2000 | Johnson et al. |
| 6,042,589 A | 3/2000 | Marianne |
| 6,056,722 A | 5/2000 | Jayaraman |
| 6,063,111 A | 5/2000 | Hieshima et al. |
| 6,066,155 A | 5/2000 | Amann et al. |
| 6,068,655 A | 5/2000 | Seguin et al. |
| 6,070,589 A | 6/2000 | Keith et al. |
| 6,090,063 A | 7/2000 | Makower et al. |
| 6,090,136 A | 7/2000 | McDonald et al. |
| 6,102,942 A | 8/2000 | Ahari |
| 6,106,530 A | 8/2000 | Harada |
| RE36,857 E | 9/2000 | Euteneuer et al. |
| 6,120,522 A | 9/2000 | Vrba et al. |
| 6,123,712 A | 9/2000 | Di Caprio et al. |
| 6,123,723 A | 9/2000 | Konya et al. |
| 6,126,685 A | 10/2000 | Lenker et al. |
| 6,129,756 A | 10/2000 | Kugler |
| 6,132,460 A | 10/2000 | Thompson |
| 6,139,572 A | 10/2000 | Campbell et al. |
| 6,143,016 A | 11/2000 | Bleam et al. |
| 6,165,167 A | 12/2000 | Delaloye |
| 6,165,210 A | 12/2000 | Lau et al. |
| 6,171,334 B1 | 1/2001 | Cox |
| 6,179,878 B1 | 1/2001 | Duerig |

| | | |
|---|---|---|
| 6,183,509 B1 | 2/2001 | Dibie |
| 6,187,034 B1 | 2/2001 | Frantzen |
| 6,190,402 B1 | 2/2001 | Horton et al. |
| 6,196,995 B1 | 3/2001 | Fagan |
| 6,200,337 B1 | 3/2001 | Moriuchi et al. |
| 6,217,585 B1 | 4/2001 | Houser et al. |
| 6,238,991 B1 | 5/2001 | Suzuki |
| 6,241,691 B1 | 6/2001 | Ferrera et al. |
| 6,241,758 B1 | 6/2001 | Cox |
| 6,248,122 B1 | 6/2001 | Klumb et al. |
| 6,251,132 B1 | 6/2001 | Ravenscroft et al. |
| 6,251,134 B1 | 6/2001 | Alt et al. |
| 6,254,612 B1 | 7/2001 | Hieshima |
| 6,254,628 B1 | 7/2001 | Wallace et al. |
| 6,258,117 B1 | 7/2001 | Camrud et al. |
| 6,264,688 B1 | 7/2001 | Herklotz et al. |
| 6,267,783 B1 | 7/2001 | Letendre et al. |
| 6,270,524 B1 | 8/2001 | Kim |
| 6,273,895 B1 | 8/2001 | Pinchuk et al. |
| 6,273,911 B1 | 8/2001 | Cox et al. |
| 6,273,913 B1 | 8/2001 | Wright et al. |
| 6,287,291 B1 | 9/2001 | Bigus et al. |
| 6,312,458 B1 | 11/2001 | Golds |
| 6,315,794 B1 | 11/2001 | Richter |
| 6,319,277 B1 | 11/2001 | Rudnick et al. |
| 6,322,586 B1 | 11/2001 | Monroe et al. |
| 6,325,823 B1 | 12/2001 | Horzewski et al. |
| 6,334,871 B1 | 1/2002 | Dor et al. |
| 6,340,366 B2 | 1/2002 | Wijay |
| 6,344,272 B1 | 2/2002 | Oldenburg et al. |
| 6,348,065 B1 | 2/2002 | Brown et al. |
| 6,350,252 B2 | 2/2002 | Ray et al. |
| 6,350,277 B1 | 2/2002 | Kocur |
| 6,357,104 B1 | 3/2002 | Myers |
| 6,361,558 B1 | 3/2002 | Hieshima et al. |
| 6,375,676 B1 | 4/2002 | Cox |
| 6,379,365 B1 | 4/2002 | Diaz |
| 6,383,171 B1 | 5/2002 | Gifford et al. |
| 6,394,995 B1 | 5/2002 | Solar et al. |
| 6,409,753 B1 | 6/2002 | Brown et al. |
| 6,415,696 B1 | 7/2002 | Erickson et al. |
| 6,416,543 B1 | 7/2002 | Hilaire et al. |
| 6,419,693 B1 | 7/2002 | Fariabi |
| 6,425,898 B1 | 7/2002 | Wilson et al. |
| 6,428,811 B1 | 8/2002 | West et al. |
| 6,451,025 B1 | 9/2002 | Jervis |
| 6,451,050 B1 | 9/2002 | Rudakov et al. |
| 6,464,720 B2 | 10/2002 | Boatman et al. |
| 6,468,298 B1 | 10/2002 | Pelton |
| 6,468,299 B2 | 10/2002 | Stack et al. |
| 6,485,510 B1 | 11/2002 | Camrud et al. |
| 6,488,694 B1 | 12/2002 | Lau et al. |
| 6,488,702 B1 | 12/2002 | Besselink |
| 6,511,468 B1 | 1/2003 | Cragg et al. |
| 6,520,986 B2 | 2/2003 | Martin et al. |
| 6,520,987 B1 | 2/2003 | Plante |
| 6,527,789 B1 | 3/2003 | Lau et al. |
| 6,527,799 B2 | 3/2003 | Shanley |
| 6,530,944 B2 | 3/2003 | West et al. |
| 6,540,777 B2 | 4/2003 | Stenzel |
| 6,551,350 B1 | 4/2003 | Thornton et al. |
| 6,555,157 B1 | 4/2003 | Hossainy |
| 6,558,415 B2 | 5/2003 | Thompson |
| 6,562,067 B2 | 5/2003 | Mathis |
| 6,569,180 B1 | 5/2003 | Sirhan et al. |
| 6,575,993 B1 | 6/2003 | Yock |
| 6,579,305 B1 | 6/2003 | Lashinski |
| 6,579,309 B1 | 6/2003 | Loos et al. |
| 6,582,394 B1 | 6/2003 | Reiss et al. |
| 6,582,460 B1 | 6/2003 | Cryer |
| 6,585,756 B1 | 7/2003 | Strecker |
| 6,589,273 B1 | 7/2003 | McDermott |
| 6,592,549 B2 | 7/2003 | Gerdts et al. |
| 6,599,296 B1 | 7/2003 | Gillick et al. |
| 6,599,314 B2 | 7/2003 | Mathis |
| 6,602,226 B1 | 8/2003 | Smith et al. |
| 6,602,282 B1 | 8/2003 | Yan |
| 6,605,062 B1 | 8/2003 | Hurley et al. |
| 6,605,109 B2 | 8/2003 | Fiedler |
| 6,607,553 B1 | 8/2003 | Healy et al. |
| 6,613,074 B1 | 9/2003 | Mitelberg et al. |
| 6,629,992 B2 | 10/2003 | Bigus et al. |
| 6,645,547 B1 | 11/2003 | Shekalim et al. |
| 6,656,212 B2 | 12/2003 | Ravenscroft et al. |
| 6,660,031 B2 | 12/2003 | Tran et al. |
| 6,660,381 B2 | 12/2003 | Halas et al. |
| 6,663,660 B2 | 12/2003 | Dusbabek et al. |
| 6,666,883 B1 | 12/2003 | Seguin et al. |
| 6,676,693 B1 | 1/2004 | Belding et al. |
| 6,676,695 B2 | 1/2004 | Solem |
| 6,679,909 B2 | 1/2004 | McIntosh et al. |
| 6,685,730 B2 | 2/2004 | West et al. |
| 6,692,465 B2 | 2/2004 | Kramer |
| 6,699,280 B2 | 3/2004 | Camrud et al. |
| 6,699,281 B2 | 3/2004 | Vallana et al. |
| 6,699,724 B1 | 3/2004 | West et al. |
| 6,702,843 B1 | 3/2004 | Brown |
| 6,709,379 B1 | 3/2004 | Brandau et al. |
| 6,709,440 B2 | 3/2004 | Callol et al. |
| 6,712,827 B2 | 3/2004 | Ellis et al. |
| 6,712,845 B2 | 3/2004 | Hossainy |
| 6,723,071 B2 | 4/2004 | Gerdts et al. |
| 6,743,219 B1 | 6/2004 | Dwyer et al. |
| 6,743,251 B1 | 6/2004 | Eder |
| 6,761,734 B2 | 7/2004 | Suhr |
| 6,776,771 B2 | 8/2004 | van Moorlegem et al. |
| 6,778,316 B2 | 8/2004 | Halas et al. |
| 6,790,227 B2 | 9/2004 | Burgermeister |
| 6,800,065 B2 | 10/2004 | Duane et al. |
| 6,825,203 B2 | 11/2004 | Pasternak et al. |
| 6,837,901 B2 | 1/2005 | Rabkin et al. |
| 6,849,084 B2 | 2/2005 | Rabkin et al. |
| 6,852,252 B2 | 2/2005 | Halas et al. |
| 6,855,125 B2 | 2/2005 | Shanley |
| 6,858,034 B1 | 2/2005 | Hijlkema et al. |
| 6,878,161 B2 | 4/2005 | Lenker |
| 6,884,257 B1 | 4/2005 | Cox |
| 6,893,417 B2 | 5/2005 | Gribbons et al. |
| 6,896,695 B2 | 5/2005 | Mueller et al. |
| 6,899,728 B1 | 5/2005 | Phillips et al. |
| 6,913,619 B2 | 7/2005 | Brown et al. |
| 6,918,928 B2 | 7/2005 | Wolinsky et al. |
| 6,939,376 B2 | 9/2005 | Shulz et al. |
| 6,945,989 B1 | 9/2005 | Betelia et al. |
| 6,945,995 B2 | 9/2005 | Nicholas |
| 6,951,053 B2 | 10/2005 | Padilla et al. |
| 6,962,603 B1 | 11/2005 | Brown et al. |
| 6,964,676 B1 | 11/2005 | Gerberding et al. |
| 6,991,646 B2 | 1/2006 | Cierc et al. |
| 7,005,454 B2 | 2/2006 | Brocchini et al. |
| 7,022,132 B2 | 4/2006 | Kocur |
| 7,029,493 B2 | 4/2006 | Majercak et al. |
| 7,037,327 B2 | 5/2006 | Salmon et al. |
| 7,090,694 B1 | 8/2006 | Morris et al. |
| 7,101,840 B2 | 9/2006 | Brocchini et al. |
| 7,131,993 B2 | 11/2006 | Gregorich |
| 7,141,063 B2 | 11/2006 | White et al. |
| 7,147,655 B2 | 12/2006 | Chermoni |
| 7,147,656 B2 | 12/2006 | Andreas et al. |
| 7,169,174 B2 | 1/2007 | Fischell et al. |
| 7,172,620 B2 | 2/2007 | Gilson |
| 7,175,654 B2 | 2/2007 | Bonsignore et al. |
| 7,182,779 B2 | 2/2007 | Acosta et al. |
| 7,192,440 B2 | 3/2007 | Andreas et al. |
| 7,208,002 B2 | 4/2007 | Shelso |
| 7,220,275 B2 | 5/2007 | Davidson et al. |
| 7,220,755 B2 | 5/2007 | Betts et al. |
| 7,223,283 B2 | 5/2007 | Chouinard |
| 7,238,197 B2 | 7/2007 | Sequin et al. |
| 7,270,668 B2 | 9/2007 | Andreas et al. |
| 7,294,146 B2 * | 11/2007 | Chew et al. .................. 623/1.12 |
| 7,314,480 B2 | 1/2008 | Eidenschink et al. |
| 7,320,702 B2 | 1/2008 | Hammersmark et al. |
| 7,323,006 B2 | 1/2008 | Andreas et al. |
| 7,534,449 B2 | 5/2009 | Saltzman et al. |
| 7,699,886 B2 | 4/2010 | Sugimoto |
| 7,918,881 B2 | 4/2011 | Andreas et al. |
| 7,993,388 B2 | 8/2011 | Lee et al. |

| | | |
|---|---|---|
| 8,257,427 B2 | 9/2012 | Andersen et al. |
| 8,317,850 B2 | 11/2012 | Kusleika |
| 2001/0020154 A1 | 9/2001 | Bigus et al. |
| 2001/0020173 A1 | 9/2001 | Klumb et al. |
| 2001/0020181 A1 | 9/2001 | Layne |
| 2001/0035902 A1 | 11/2001 | Iddan et al. |
| 2001/0044595 A1 | 11/2001 | Reydel et al. |
| 2001/0044632 A1 | 11/2001 | Daniel et al. |
| 2001/0049547 A1 | 12/2001 | Moore |
| 2002/0007212 A1 | 1/2002 | Brown et al. |
| 2002/0037358 A1 | 3/2002 | Barry et al. |
| 2002/0045914 A1 | 4/2002 | Roberts et al. |
| 2002/0052642 A1 | 5/2002 | Cox et al. |
| 2002/0087186 A1 | 7/2002 | Shelso |
| 2002/0091439 A1 | 7/2002 | Baker et al. |
| 2002/0092536 A1 | 7/2002 | LaFontaine et al. |
| 2002/0107560 A1 | 8/2002 | Richter |
| 2002/0111671 A1 | 8/2002 | Stenzel |
| 2002/0123786 A1 | 9/2002 | Gittings et al. |
| 2002/0128706 A1 | 9/2002 | Osypka |
| 2002/0138132 A1 | 9/2002 | Brown |
| 2002/0151924 A1 | 10/2002 | Shiber |
| 2002/0151955 A1 | 10/2002 | Tran et al. |
| 2002/0156496 A1 | 10/2002 | Chermoni |
| 2002/0165599 A1 | 11/2002 | Nasralla |
| 2002/0168317 A1 | 11/2002 | Daighighian et al. |
| 2002/0177890 A1 | 11/2002 | Lenker |
| 2002/0183763 A1 | 12/2002 | Callol et al. |
| 2002/0188343 A1 | 12/2002 | Mathis |
| 2002/0188347 A1 | 12/2002 | Mathis |
| 2002/0193873 A1 | 12/2002 | Brucker et al. |
| 2003/0045923 A1 | 3/2003 | Bashiri et al. |
| 2003/0093143 A1 | 5/2003 | Zhao et al. |
| 2003/0097169 A1 | 5/2003 | Brucker et al. |
| 2003/0114912 A1 | 6/2003 | Sequin et al. |
| 2003/0114919 A1 | 6/2003 | McQuiston et al. |
| 2003/0114922 A1 | 6/2003 | Iwasaka et al. |
| 2003/0125791 A1 | 7/2003 | Sequin et al. |
| 2003/0125800 A1 | 7/2003 | Shulze et al. |
| 2003/0125802 A1 | 7/2003 | Callol et al. |
| 2003/0135259 A1 | 7/2003 | Simso |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0139798 A1 | 7/2003 | Brown et al. |
| 2003/0163085 A1 | 8/2003 | Tanner et al. |
| 2003/0163155 A1 | 8/2003 | Haverkost et al. |
| 2003/0176909 A1 | 9/2003 | Kusleika |
| 2003/0191516 A1 | 10/2003 | Weldon et al. |
| 2003/0195609 A1 | 10/2003 | Berenstein |
| 2003/0199821 A1 | 10/2003 | Gerdts et al. |
| 2003/0204238 A1 | 10/2003 | Tedeschi |
| 2003/0208223 A1 | 11/2003 | Kleiner |
| 2003/0212447 A1 | 11/2003 | Euteneuer |
| 2003/0225446 A1 | 12/2003 | Hartley |
| 2004/0015224 A1 | 1/2004 | Armstrong et al. |
| 2004/0024450 A1 | 2/2004 | Shulze et al. |
| 2004/0030380 A1 | 2/2004 | Shulze et al. |
| 2004/0044395 A1 | 3/2004 | Nelson |
| 2004/0073290 A1 | 4/2004 | Chouinard |
| 2004/0087965 A1 | 5/2004 | Levine et al. |
| 2004/0088044 A1 | 5/2004 | Brown et al. |
| 2004/0093061 A1* | 5/2004 | Acosta et al. ................. 623/1.11 |
| 2004/0093067 A1 | 5/2004 | Israel |
| 2004/0098081 A1 | 5/2004 | Landreville et al. |
| 2004/0106979 A1 | 6/2004 | Goicoechea et al. |
| 2004/0111145 A1 | 6/2004 | Serino et al. |
| 2004/0117008 A1 | 6/2004 | Wnendt et al. |
| 2004/0143322 A1 | 7/2004 | Litvack et al. |
| 2004/0176832 A1 | 9/2004 | Hartley et al. |
| 2004/0181239 A1 | 9/2004 | Dorn et al. |
| 2004/0186551 A1 | 9/2004 | Kao et al. |
| 2004/0193245 A1 | 9/2004 | Deem et al. |
| 2004/0215165 A1 | 10/2004 | Coyle et al. |
| 2004/0215312 A1 | 10/2004 | Andreas et al. |
| 2004/0215331 A1 | 10/2004 | Chew et al. |
| 2004/0230285 A1 | 11/2004 | Gifford, III et al. |
| 2004/0243217 A1 | 12/2004 | Andersen et al. |
| 2004/0249434 A1 | 12/2004 | Andreas et al. |
| 2004/0249435 A1 | 12/2004 | Andreas et al. |
| 2004/0249439 A1 | 12/2004 | Richter et al. |
| 2005/0004657 A1 | 1/2005 | Burgermeister |
| 2005/0010276 A1 | 1/2005 | Acosta et al. |
| 2005/0038494 A1 | 2/2005 | Eidenschink |
| 2005/0038505 A1 | 2/2005 | Shuize et al. |
| 2005/0049673 A1 | 3/2005 | Andreas et al. |
| 2005/0080474 A1 | 4/2005 | Andreas et al. |
| 2005/0080475 A1 | 4/2005 | Andreas et al. |
| 2005/0085897 A1 | 4/2005 | Bonsignore |
| 2005/0090846 A1 | 4/2005 | Pedersen et al. |
| 2005/0123451 A1 | 6/2005 | Nomura |
| 2005/0125051 A1 | 6/2005 | Eidenschink et al. |
| 2005/0131008 A1 | 6/2005 | Betts et al. |
| 2005/0133164 A1 | 6/2005 | Fischer et al. |
| 2005/0137622 A1 | 6/2005 | Griffin |
| 2005/0143827 A1 | 6/2005 | Globerman et al. |
| 2005/0149159 A1 | 7/2005 | Andreas et al. |
| 2005/0149168 A1 | 7/2005 | Gregorich |
| 2005/0165378 A1 | 7/2005 | Heinrich et al. |
| 2005/0171568 A1 | 8/2005 | Duffy |
| 2005/0182477 A1 | 8/2005 | White |
| 2005/0209674 A1 | 9/2005 | Kutscher et al. |
| 2005/0209676 A1 | 9/2005 | Kusleika |
| 2005/0209680 A1 | 9/2005 | Gale et al. |
| 2005/0222671 A1 | 10/2005 | Schaeffer et al. |
| 2005/0228477 A1 | 10/2005 | Grainger et al. |
| 2005/0245637 A1 | 11/2005 | Hossainy et al. |
| 2005/0249777 A1 | 11/2005 | Michal et al. |
| 2005/0278011 A1 | 12/2005 | Peckham |
| 2005/0288763 A1 | 12/2005 | Andreas et al. |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0173529 A1* | 8/2006 | Blank ........................ 623/1.16 |
| 2006/0200223 A1 | 9/2006 | Andreas et al. |
| 2006/0206190 A1 | 9/2006 | Chermoni |
| 2006/0229700 A1 | 10/2006 | Acosta et al. |
| 2006/0229706 A1 | 10/2006 | Shulze et al. |
| 2006/0271150 A1 | 11/2006 | Andreas et al. |
| 2006/0271151 A1 | 11/2006 | McGarry et al. |
| 2006/0282147 A1 | 12/2006 | Andreas |
| 2006/0282149 A1 | 12/2006 | Kao |
| 2006/0282150 A1 | 12/2006 | Olson et al. |
| 2006/0287726 A1 | 12/2006 | Segal et al. |
| 2007/0010869 A1 | 1/2007 | Sano |
| 2007/0027521 A1 | 2/2007 | Andreas et al. |
| 2007/0043419 A1 | 2/2007 | Nikolchev et al. |
| 2007/0067012 A1 | 3/2007 | George et al. |
| 2007/0088368 A1 | 4/2007 | Acosta et al. |
| 2007/0088420 A1 | 4/2007 | Andreas et al. |
| 2007/0088422 A1 | 4/2007 | Chew et al. |
| 2007/0100423 A1 | 5/2007 | Acosta et al. |
| 2007/0100424 A1 | 5/2007 | Chew et al. |
| 2007/0106365 A1 | 5/2007 | Andreas et al. |
| 2007/0118202 A1 | 5/2007 | Chermoni |
| 2007/0118203 A1 | 5/2007 | Chermoni |
| 2007/0118204 A1 | 5/2007 | Chermoni |
| 2007/0129733 A1 | 6/2007 | Will et al. |
| 2007/0135906 A1 | 6/2007 | Badylak et al. |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0219612 A1 | 9/2007 | Andreas et al. |
| 2007/0219613 A1 | 9/2007 | Kao et al. |
| 2007/0265637 A1 | 11/2007 | Andreas et al. |
| 2007/0270936 A1 | 11/2007 | Andreas et al. |
| 2007/0276461 A1 | 11/2007 | Andreas et al. |
| 2007/0281117 A1 | 12/2007 | Kaplan et al. |
| 2007/0292518 A1 | 12/2007 | Ludwig |
| 2008/0004690 A1 | 1/2008 | Robaina |
| 2008/0046067 A1 | 2/2008 | Toyokawa |
| 2008/0071345 A1 | 3/2008 | Hammersmark et al. |
| 2008/0077229 A1 | 3/2008 | Andreas et al. |
| 2008/0091257 A1 | 4/2008 | Andreas et al. |
| 2008/0097299 A1 | 4/2008 | Andreas et al. |
| 2008/0097574 A1 | 4/2008 | Andreas et al. |
| 2008/0125850 A1 | 5/2008 | Andreas et al. |
| 2008/0132989 A1 | 6/2008 | Snow et al. |

| | | |
|---|---|---|
| 2008/0147162 A1 | 6/2008 | Andreas et al. |
| 2008/0177369 A1 | 7/2008 | Will et al. |
| 2008/0199510 A1 | 8/2008 | Ruane et al. |
| 2008/0208311 A1 | 8/2008 | Kao et al. |
| 2008/0208318 A1 | 8/2008 | Kao et al. |
| 2008/0234798 A1 | 9/2008 | Chew et al. |
| 2008/0234799 A1 | 9/2008 | Acosta et al. |
| 2008/0243225 A1 | 10/2008 | Satasiya et al. |
| 2008/0249607 A1 | 10/2008 | Webster et al. |
| 2008/0269865 A1 | 10/2008 | Snow et al. |
| 2009/0076584 A1 | 3/2009 | Mao et al. |
| 2009/0105686 A1 | 4/2009 | Snow et al. |
| 2009/0149863 A1 | 6/2009 | Andreas et al. |
| 2009/0234428 A1 | 9/2009 | Snow et al. |
| 2009/0248137 A1 | 10/2009 | Andersen et al. |
| 2009/0248140 A1 | 10/2009 | Gerberding |
| 2009/0264979 A1 | 10/2009 | Kao et al. |
| 2009/0276030 A1 | 11/2009 | Kusleika |
| 2010/0004729 A1 | 1/2010 | Chew et al. |

FOREIGN PATENT DOCUMENTS

| | | |
|---|---|---|
| DE | 199 50 756 | 8/2000 |
| DE | 101 03 000 | 8/2002 |
| EP | 203945 B2 | 12/1986 |
| EP | 274129 B1 | 7/1988 |
| EP | 282143 | 9/1988 |
| EP | 0 364 787 A1 | 4/1990 |
| EP | 0 505 686 | 9/1992 |
| EP | 0 533 960 | 3/1993 |
| EP | 0 696 447 A2 | 2/1996 |
| EP | 0 714 640 | 6/1996 |
| EP | 0 797 963 A2 | 1/1997 |
| EP | 0 596 145 | 5/1997 |
| EP | 947180 | 10/1999 |
| EP | 1 254 644 A1 | 11/2002 |
| EP | 1 258 230 | 11/2002 |
| EP | 1 277 449 | 1/2003 |
| EP | 1 290 987 A2 | 3/2003 |
| EP | 1 318 765 | 6/2003 |
| EP | 1 470 834 | 10/2004 |
| EP | 1 523 959 A2 | 4/2005 |
| EP | 1 523 960 A2 | 4/2005 |
| EP | 1266638 B1 | 10/2005 |
| GB | 2277875 A | 11/1994 |
| JP | 03-133446 | 6/1991 |
| JP | 07-132148 | 5/1995 |
| JP | 10-503663 | 4/1998 |
| JP | 10-295823 | 11/1998 |
| JP | 11-503056 T | 3/1999 |
| JP | 2935561 B2 | 8/1999 |
| JP | 2001-190687 | 7/2001 |
| JP | 2002-538932 T | 11/2002 |
| JP | 2004-121343 A | 4/2004 |
| WO | WO 94/27687 A1 | 12/1994 |
| WO | 95/29647 A2 | 11/1995 |
| WO | 96/26689 | 9/1996 |
| WO | WO 96/33677 | 10/1996 |
| WO | WO 95/26695 A1 | 11/1996 |
| WO | WO96/37167 A1 | 12/1996 |
| WO | WO 96/39077 | 12/1996 |
| WO | 97/10778 | 3/1997 |
| WO | WO 97/46174 | 12/1997 |
| WO | WO 97/48351 | 12/1997 |
| WO | 98/20810 | 5/1998 |
| WO | WO 98/37833 | 9/1998 |
| WO | 98/58600 | 12/1998 |
| WO | WO 99/01087 A1 | 1/1999 |
| WO | 99/65421 | 12/1999 |
| WO | WO 00/12832 A3 | 3/2000 |
| WO | WO 00/15151 A1 | 3/2000 |
| WO | WO 00/25841 | 5/2000 |
| WO | WO 00/32136 A1 | 6/2000 |
| WO | WO 00/41649 A1 | 7/2000 |
| WO | WO 00/50116 | 8/2000 |
| WO | WO 00/51525 A1 | 9/2000 |
| WO | WO 00/56237 | 9/2000 |
| WO | WO 00/62708 | 10/2000 |
| WO | WO 00/72780 | 12/2000 |
| WO | 01/26707 | 4/2001 |
| WO | 01/34063 | 5/2001 |
| WO | WO 01/70297 | 9/2001 |
| WO | WO 01/91918 | 12/2001 |
| WO | 02/071975 | 9/2002 |
| WO | WO 02/085253 | 10/2002 |
| WO | WO 02/098326 | 12/2002 |
| WO | WO 03/022178 A1 | 3/2003 |
| WO | WO 03/047651 | 6/2003 |
| WO | WO 03/051425 | 6/2003 |
| WO | WO 03/075797 | 9/2003 |
| WO | WO 2004/017865 | 3/2004 |
| WO | WO 2004/043299 | 5/2004 |
| WO | WO 2004/043301 | 5/2004 |
| WO | WO 2004/043510 | 5/2004 |
| WO | WO 2004/052237 | 6/2004 |
| WO | 2004/087006 | 10/2004 |
| WO | 2004/091441 | 10/2004 |
| WO | WO 2005/009295 | 2/2005 |
| WO | WO 2005/013853 | 2/2005 |
| WO | 2005/023153 | 3/2005 |
| WO | 2006036939 | 4/2006 |
| WO | 2006/047520 | 5/2006 |
| WO | 2007/035805 | 3/2007 |
| WO | WO 2007/053187 | 5/2007 |
| WO | WO 2007/146411 | 12/2007 |
| WO | WO 2008/005111 | 1/2008 |

OTHER PUBLICATIONS

Evans Analytical Group, "Functional Sites on Non-polymeric Materials: Gas Plasma Treatment and Surface Analysis," http://www.eaglabs.com.

Joung et al., "Estrogen Release from Metallic Stent Surface for the Prevention of Restenosis," Journal of Controlled Release 92 (2003) pp. 83-91.

Supplementary European Search Report of EP Patent Application No. 05727731.1, dated Mar. 25, 2008, 2 pages total.

Supplementary European Search Report of EP Patent Application No. 05744136, dated Mar. 26, 2008, 3 pages total.

U.S. Appl. No. 60/336,607, filed Dec. 3, 2001, first named inventor: Bernard Andreas.

U.S. Appl. No. 60/336,767, filed Dec. 3, 2001, first named inventor: Bernard Andreas.

U.S. Appl. No. 60/336,967, filed Dec. 3, 2001, first named inventor: Sunmi Chew.

U.S. Appl. No. 60/364,389, filed Mar. 13, 2002, first named inventor: Sunmi Chew.

U.S. Appl. No. 60/440,839, filed Jan. 17, 2003, first named inventor: Bernard Andreas.

U.S. Appl. No. 60/561,041, filed Apr. 9, 2004, first named inventor: Jeffry Grainger.

U.S. Appl. No. 60/784,309, filed Mar. 20, 2006, first named inventor: Bernard Andreas.

U.S. Appl. No. 60/810,522, filed Jun. 2, 2006, first named inventor: Stephen Kaplan.

U.S. Appl. No. 60/890,703, filed Feb. 20, 2007, first named inventor: Patrick Ruane.

U.S. Appl. No. 61/012,317, filed Dec. 7, 2007, first named inventor: Patrick Ruane.

U.S. Appl. No. 09/097,855, filed Jun. 15, 1998, first named inventor: Enrique J. Klein; Abandoned.

U.S. Appl. No. 09/225,364, filed Jan. 4, 1999, first named inventor: Aaron V. Kaplan; abandoned.

U.S. Appl. No. 10/874,859, filed Jun. 22, 2004, first named inventor: Pablo Acosta. Abandoned.

U.S. Appl. No. 11/462,951, filed Aug. 7, 2006, first named inventor: David Snow.

U.S. Appl. No. 11/689,927, filed Mar. 22, 2007, first named inventor: David Snow.

U.S. Appl. No. 11/771,929, filed Jun. 29, 2007, first named inventor: David Snow.

U.S. Appl. No. 11/857,562, filed Sep. 19, 2007, first named inventor: Bryan Mao.

U.S. Appl. No. 11/938,730, filed Nov. 12, 2007, first named inventor: Sunmi Chew; abandoned.

U.S. Appl. No. 12/033,586, filed Feb. 19, 2008, first named inventor: Patrick H. Ruane.
U.S. Appl. No. 12/040,598, filed Feb. 29, 2008, first named inventor: Bernard Andreas.
U.S. Appl. No. 12/043,513, filed Mar. 6, 2008, first named inventor: David Lowe.
U.S. Appl. No. 12/057,527, filed Mar. 28, 2008, first named inventor: Allan Will.
U.S. Appl. No. 12/061,951, filed Apr. 3, 2008, first named inventor: Stephen Kao.
U.S. Appl. No. 12/109,477, filed Apr. 25, 2008, first named inventor: Stephen Kao.
U.S. Appl. No. 12/127,147, filed May 27, 2008, first named inventor: Sunmi Chew.
U.S. Appl. No. 12/133,909, filed Jun. 5, 2008, first named inventor: David Sanderson.
Columbo, "The Invatec Bifurcation Stent Solution" Bifurcation Stents: Novel Solutions, TCT 2003, Washington: Sep. 15-18, 2003, 24 pages total.
Cooley et al., "Applications of Ink-Jet Printing Technology to BioMEMs and Microfluidic Systems," Proceedings, SPIE Conference on Microfluidics and BioMEMs, (Oct. 2001).
Lefevre et al. "Approach to Coronary Bifurcation Stenting in 2003," Euro PCR, (May 2003) 28 pages total.
"Stent". Definitions from Dictionary.com. Unabridged 9v1.01). Retrieved Sep. 22, 2006, from Dictionary.com website: <http://dictionary.reference.com/search?q=stent>.
Stimpson et al., Parallel Production of Oligonucleotide Arrays Using Membranes and Reagent Jet Printing, BioTechniques 25:886-890 (Nov. 1998).
Supplementary European Search Report of EP Patent Application No. 07758831, dated Dec. 14, 2009.
Chu et al., "Preparation of Thermo-Responsive Core-Shell Microcapsules with a Porous Membrane and Poly(N-isopropylactylamide) Gates,"J Membrane Sci. Oct. 15, 2001; 192(1-2):27-39.
"Drug Delivery Stent With Holes Located on Neutral Axis" Research Disclosure, Kenneth Mason Publications, Hampshire, CB, No. 429, Jan. 2000, p. 13.
Tilley, "Biolimus A9-Eluting Stent Shows Promise," Medscape Medical News, Oct. 5, 2004; retrieved from the internet: <http://www.medscape.com/viewarticle/490621>, 2 pages total.
Weir et al., "Degradation of poly-L-lactide. Part 2: increased temperature accelerated degradation," Proc Inst Mech Eng H. 2004;218(5):321-30.

* cited by examiner

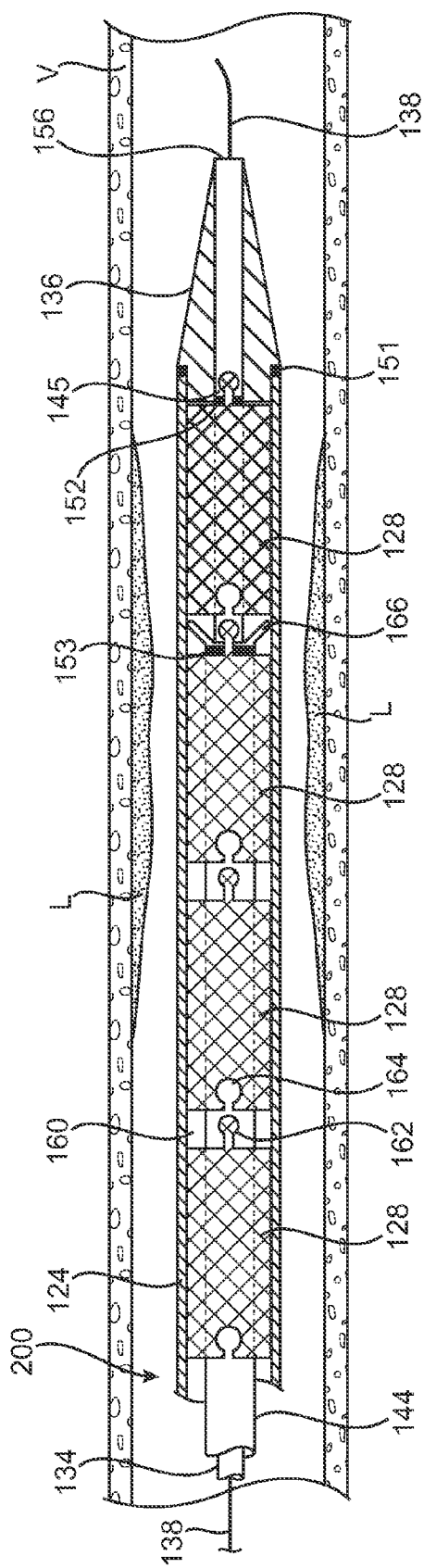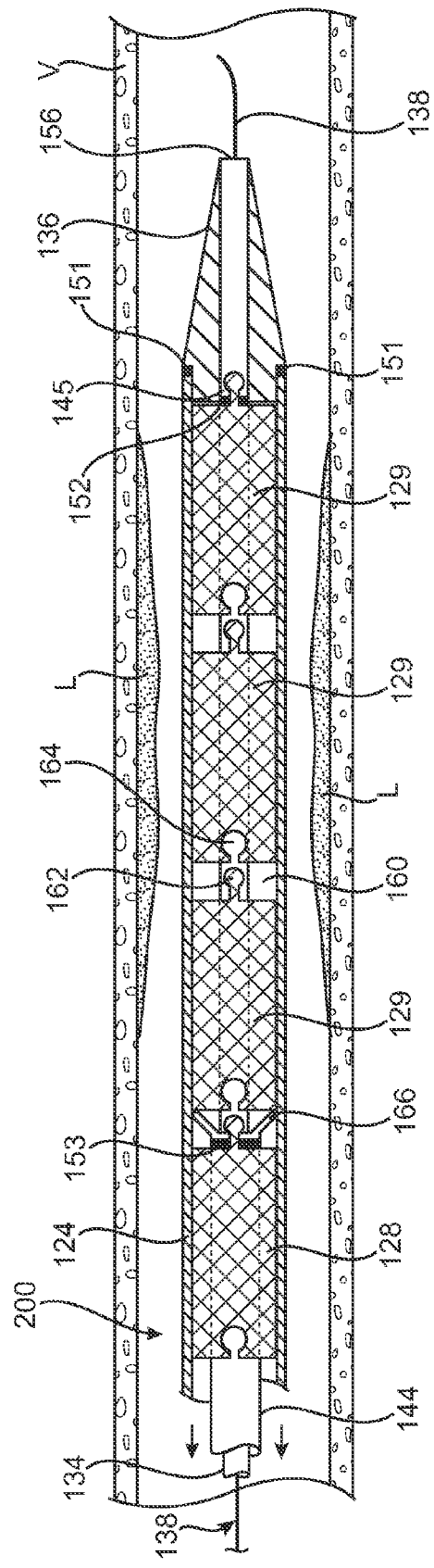

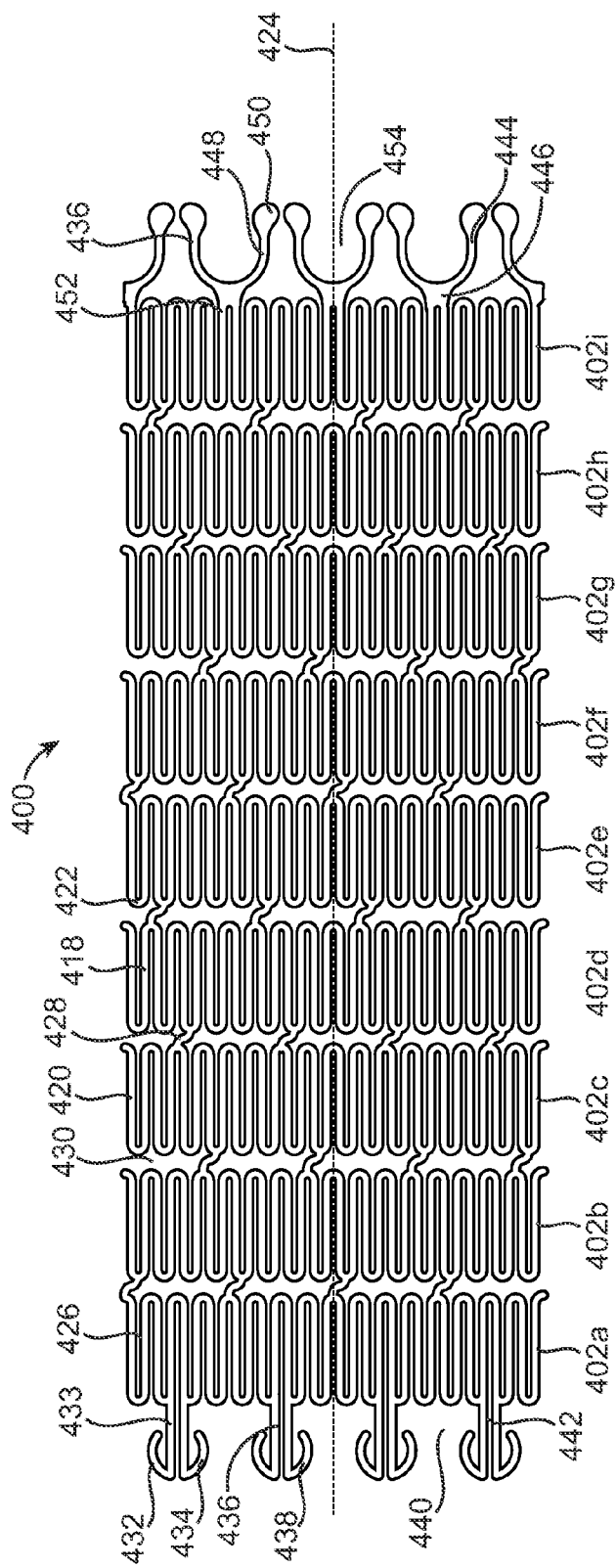
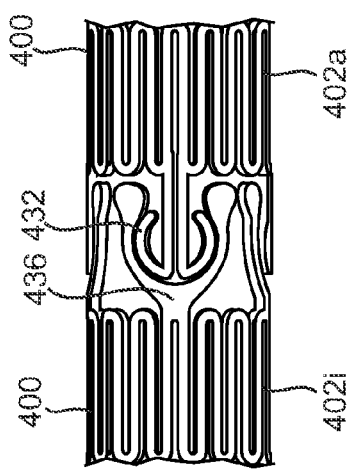
FIG. 4A
FIG. 4B

DEVICES AND METHODS FOR CONTROLLING EXPANDABLE PROSTHESES DURING DEPLOYMENT

CROSS-REFERENCES TO RELATED APPLICATIONS

NOT APPLICABLE

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

1. Field of the Invention

This invention relates generally to medical apparatus and methods, and more specifically to vascular catheters, stents and stent delivery systems for use in the coronary and peripheral arteries as well as other vessels and body lumens.

Stenting is an important treatment option for patients with occlusive disease in the vasculature as well as other systems such as the biliary tract. The stenting procedure involves placing a tubular prosthesis at the site of a lesion, typically within a diseased artery. The procedure is performed in order to maintain the patency of the artery and is often performed after a primary treatment such as angioplasty. Early stent results suffered from high rates of restenosis, i.e. the tendency for the stented vessel, such as an artery, to become re-occluded following stent implantation. However, in recent years, restenosis rates have decreased substantially, due to many improvements in stent delivery, stent technology as well as the use of drugs. As a result, the number of stent related procedures being performed worldwide continues to dramatically increase.

Stents are typically either self-expanding or balloon expandable and they are delivered to the arteries using long, flexible vascular catheters typically inserted percutaneously through the patient's femoral artery. For balloon expandable stents, the stents are usually mounted over a balloon on the delivery catheter, thus, when the balloon is inflated, it expands which correspondingly expands and deforms the stent to the desired diameter. The balloon can then be deflated and removed, leaving the stent in place. For self-expanding stents, the stent is released from the delivery catheter and it resiliently expands into engagement with the vessel wall. Self-expanding stents are often used in the peripheral vascular system since they are more resilient than balloon expandable stents. Resilient stents are better suited for implantation into regions of the body closer to the body's surface, such as a peripheral artery, since the stent's resilience helps minimize damage or crushing caused by body movement or externally applied forces.

Self-expanding stents may also be used in the coronary arteries and may provide advantages over balloon expandable stents. Balloon expandable stents are typically expanded with a balloon having a constant diameter and therefore the expanded stent may not conform well to a coronary artery having variations in diameter due to tortuosity or taper. Therefore, there is a potential for gaps between the outer stent surface and the inner surface of the artery wall. These gaps may lead to thrombus formation and recently, there has been concern that this effect is pronounced in drug eluting stents because the drug delays endothelialization of the stent surface, allowing the gaps to remain for a longer period of time. Self-expanding stents expand until the outer stent surface is constrained by contact with a vessel wall. Therefore, gaps between the stent and the arterial wall are minimized thus helping to reduce thrombus formation. Companies such as Devax (Irvine, Calif.) and Cardiomind (Sunnyvale, Calif.) are developing self-expanding stents for implantation into the coronary arteries.

Current stent delivery technology suffers from a number of drawbacks which can make delivery of stents challenging. In particular, current stent delivery catheters often employ stents having fixed lengths. The proper selection of fixed length stents requires accurate knowledge of the lesion length being treated. While lesion length may be measured prior to stent deployment using angiography and fluoroscopy, these measurements are often inaccurate. Thus, if an incorrectly sized stent is introduced to a treatment site, it must be removed from the patient along with the delivery catheter and replaced with a different device having the correct stent size. This prolongs the procedure, increases waste and results in a more costly procedure.

Additionally, and especially in the case of peripheral vascular disease, lesions are often long and diffuse. A single long stent may be deployed to treat a single lesion or to span multiple lesions, however this is not optimal since longer stents tend to have higher fracture and restenosis rates as compared with shorter stents. Therefore, placement of multiple shorter stents in a long lesion may be advantageous instead of deploying a single long length stent.

The use of "custom length" stents as an alternative to fixed length stents has been proposed. One such approach for providing a custom length stent has been to use segmented stents for treatment in which only some of the stents are deployed for treatment. Several exemplary systems are described in several copending, commonly assigned applications which are listed below. In these systems, the stent segments are deployed by selective advancement over the delivery catheter. After delivering an initial group of segments, the catheter may be repositioned to a new treatment site and a further group of segments can then be deployed. These systems enable treatment of multiple lesions with a single device and may contain up to fifty segments.

While this technology represents a significant improvement over earlier stent delivery systems, in the case of self-expanding stents, accurate delivery of the stents to a treatment site can present other challenges. Because self-expanding stent segments tend to rapidly spring open upon deployment, it is difficult to control their placement. In some cases, the stents may actually eject or "watermelon seed" away from the delivery catheter. Therefore, a delivery system that allows more precise control of stent deployment and placement is desirable.

Another challenge with existing "custom length" stent delivery systems is that to deliver multiple stent segments to multiple lesion sites requires an intricate delivery system that can be somewhat complex to use. Thus, a simpler delivery system that allows length customization is desirable, especially for use in treating long lesions in the peripheral and coronary vasculature.

For the reasons above, as well as others, it would be desirable to provide improved prosthetic stents and delivery catheters. It would be particularly desirable to provide catheters which enable stent length to be customized using multiple stent segments. It is also desirable to provide a delivery system that is flexible and can track torturous vessels and that has a simple construction and is less costly and easy to use in deploying a selectable number of stent segments to a treatment site. It is further desirable to provide a stent delivery catheter that can control the delivery and placement of self-expanding stents in the peripheral and coronary vascular system.

2. Description of the Background Art

Prior publications describing catheters for delivering multiple segmented stents include: U.S. Publication Nos. 2004/0098081, 2005/0149159, 2004/0093061, 2005/0010276, 2005/0038505, 2004/0186551 and 2003/013266. Prior related unpublished co-pending U.S. patent applications include Ser. No. 11/148,713, filed Jun. 8, 2005, entitled "Devices and Methods for Operating and Controlling Interventional Apparatus"; Ser. No. 11/148,545, filed Jun. 8, 2005, entitled "Apparatus and Methods for Deployment of Multiple Custom-Length Prosthesis"; Ser. No. 11/344,464, filed Jan. 30, 2006, entitled "Apparatus and Methods for Deployment of Custom-Length Prostheses"; Ser. No. 60/784,309, filed Mar. 20, 2006, entitled "Apparatus and Methods for Deployment of Linked Prosthetic Segments"; Ser. No. 11/469,773 filed Sep. 1, 2006, entitled "Custom Length Stent Apparatus"; and Ser. No. 11/462,951, filed Aug. 7, 2006, entitled "Custom Length Stent Apparatus." The full disclosures of each of these patents and applications are incorporated herein by reference.

BRIEF SUMMARY OF THE INVENTION

The invention generally provides for the delivery of self-expanding prostheses with a flexible delivery catheter capable of navigating vessels such as the peripheral and coronary arteries. The delivery catheter permits controlled deployment of a selectable number of prosthetic segments at a treatment site, thus allowing customization of prosthesis length while the delivery catheter is in a body lumen at a treatment site. Customization of prosthesis length in situ permits better matching of the prosthesis length to the lesion length being treated.

The terms "stent" and "stenting" are defined to include any of the array of expandable prostheses and scaffolds which are introduced into a lumen at a target treatment site and expanded in situ thereby exerting a radially outward force against the lumen wall. The prosthesis of the present invention comprises a closed or an open lattice structure and is typically fabricated from an elastic material or self-expanding material, including superelastic materials such as nickel-titanium alloys like Nitinol, or spring temper stainless steels or polymers, and the lattice structures are commonly constrained radially during delivery and upon deployment the constraining structure is removed, allowing the prosthesis to "self-expand" at the target site. The terms "stent," "prosthesis," "prosthetic segment" and "stent segment" refer broadly to all radially expansible stents, grafts, and other scaffold-like structures which are intended for deployment within a body lumen.

In a first aspect of the present invention, a catheter for delivering a prosthesis to a treatment site in a body lumen comprises an elongate flexible member having a proximal end and a distal end. A sheath is slidably disposed over the elongate flexible member and a plurality of self-expanding tubular prostheses are carried in axially spaced-apart locations along the elongate flexible member, within the sheath. The plurality of self-expanding tubular prostheses are adapted to be selectively interlocked with one another and they are constrained by the sheath in a radially contracted configuration. The prostheses are separately releasable from the sheath as the sheath is retracted relative to the elongate flexible member.

The catheter also includes a pusher member that is slidably disposed along the elongate flexible member within the sheath and the pusher is adapted to move past the prostheses in a first direction, usually without displacing the prostheses. In a second direction, the pusher member engages a selected prosthesis and the pusher can move the prosthesis so as to interlock the selected prosthesis with a second prosthesis. The pusher member may have an engagement member which is deflectable radially inward by contact with the prostheses when moved in the first direction while in the second direction the engagement member engages the prostheses selected for deployment. Sometimes the engagement member may comprise a plurality of flexible fingers that extend radially outward from the pusher member. The pusher member often may exert substantially greater axial force against the plurality of self-expanding tubular prostheses when the pusher member is advanced distally than when the pusher member is retracted proximally.

Sometimes the catheter comprises a stopping element that is axially disposed along the elongate flexible member. The stopping element is adapted to prevent the plurality of self-expanding tubular prostheses from being displaced past the distal end of the elongate flexible member when the pusher member is advanced distally. The catheter may also comprise a handle that is usually near the proximal end of the elongate flexible member and the handle usually has a control mechanism adapted to move the sheath and pusher member. Sometimes the catheter may also include a central lumen disposed within the elongate shaft that can carry a guidewire.

In another aspect of the present invention, a method for delivering a prosthesis to a body lumen having a lesion with a length comprises introducing into the body lumen one or more self-expanding tubular prostheses. The prostheses are carried at axially spaced apart locations along an elongate flexible member and they are constrained in a contracted configuration within a sheath. Selecting a first group of the tubular prostheses for delivery picks a first group of prostheses that has a combined length substantially traversing the lesion. Bringing the first group into engagement with each other within the sheath interlocks prostheses in the first group with one another and uncovering the first group from the sheath removes the constraint from the first group so they may expand at the first treatment site while a second group of prostheses is retained within the sheath. Sometimes the method may further comprise selecting one or more additional self-expanding tubular prostheses and bringing them into to engagement with the first group within the sheath so that the additional prostheses interlock with the first group.

Selecting a first group of prostheses may comprise proximally retracting a pusher member. The pusher member often has a flexible engagement member that is deflected by the prostheses as the pusher member is retracted proximally. Bringing the first group into engagement with each other may comprise engaging at least one of the first group of prostheses with a pusher member and advancing the pusher member distally. Bringing the first group into engagement with each other may also comprise stopping the first group of prostheses from moving distally with a stopping element that is disposed on the elongate flexible member. Engaging the at least one prosthesis may include engaging the prosthesis with a flexible engagement member that is disposed on the pusher member and uncovering the first group can involve proximally retracting the sheath. The method may also comprise releasing a therapeutic agent from the first group of prostheses after expansion at the treatment site. Often, the therapeutic agent may comprise an anti-restenosis agent.

In still another aspect of the present invention, a self-expanding tubular prosthesis comprises a plurality of self-expanding tubular rings that have a plurality of axial struts and a plurality of connectors coupling adjacent struts together. The axial struts and connectors also may form a plurality of substantially parallel and spaced apart columns of open cells. The axial struts and connectors often form a substantially zig-zag pattern and a bridge member couples adjacent tubular rings together. A plurality of bridges, which may be sigmoidally shaped may join the columns of open cells or rings together. Sometimes the connectors are U-shaped and often the columns of open cells are out of phase with an adjacent column. The prosthesis is usually adapted to be interlocked with an adjacent prosthesis when pressed together and the prostheses remain interlocked with one another even after radial self-expansion. The prosthesis often may have an interlocking tab on one end of the tubular rings that is adapted to interlock with an adjacent tubular ring when the rings are pressed together.

The interlocking tab may comprise a strut that defines an aperture which is adapted to hold a radiopaque marker. The bridge may be coupled to a connector and have an axially extending strut that joins the bridge with the connector. The bridge may connect to an apex of the connector, which may be U-shaped. The interlocking tab may comprise a narrow neck region and an enlarged head region which may be C-shaped. The enlarged head region may have an arcuate strut defining a narrow inlet portion and a wider receiving portion. The receiving portion is usually adapted to receive and interlock with an interlocking tab on an adjacent ring.

The enlarged head region may have a plurality of arcuate struts that are coupled to the ring with a plurality of axial struts and the neck region may comprise a plurality of axial struts. The enlarged head region may also comprise an arcuate strut that forms a C-shape and that is coupled to the ring with an axial strut.

The prosthesis may also have a female receiving tab on an end of the prosthesis opposite of the interlocking tab. The female tab may include an arcuate strut that defines a receptacle, sometimes C-shaped, which can receive and interlock with an enlarged head of an adjacent prosthesis. The arcuate strut may be coupled to a ring with an axial strut. The female tab may also comprise an arcuate strut that defines an aperture which can hold a radiopaque marker. The prosthesis may further comprise a therapeutic agent that is carried on the prosthesis and that may be released therefrom. Often, the therapeutic agent comprises an anti-restenosis agent. The prosthesis often has an overall length in the range from about 5 mm to about 50 mm. Sometimes each of the prostheses have the same length, although sometimes at least one of the prostheses may have a different length than another of the prostheses.

These and other embodiments are described in further detail in the following description related to the appended drawing figures.

BRIEF DESCRIPTION OF THE DRAWINGS

FIGS. 2A-2E illustrate selection and deployment of prostheses in accordance with an exemplary embodiment.

FIG. 4A shows a top view of another embodiment of a prosthesis after it has been unrolled and flattened.

FIG. 4B shows interlocking of two of the prostheses illustrated in FIG. 4A.

DETAILED DESCRIPTION OF THE INVENTION

Figure 1A:
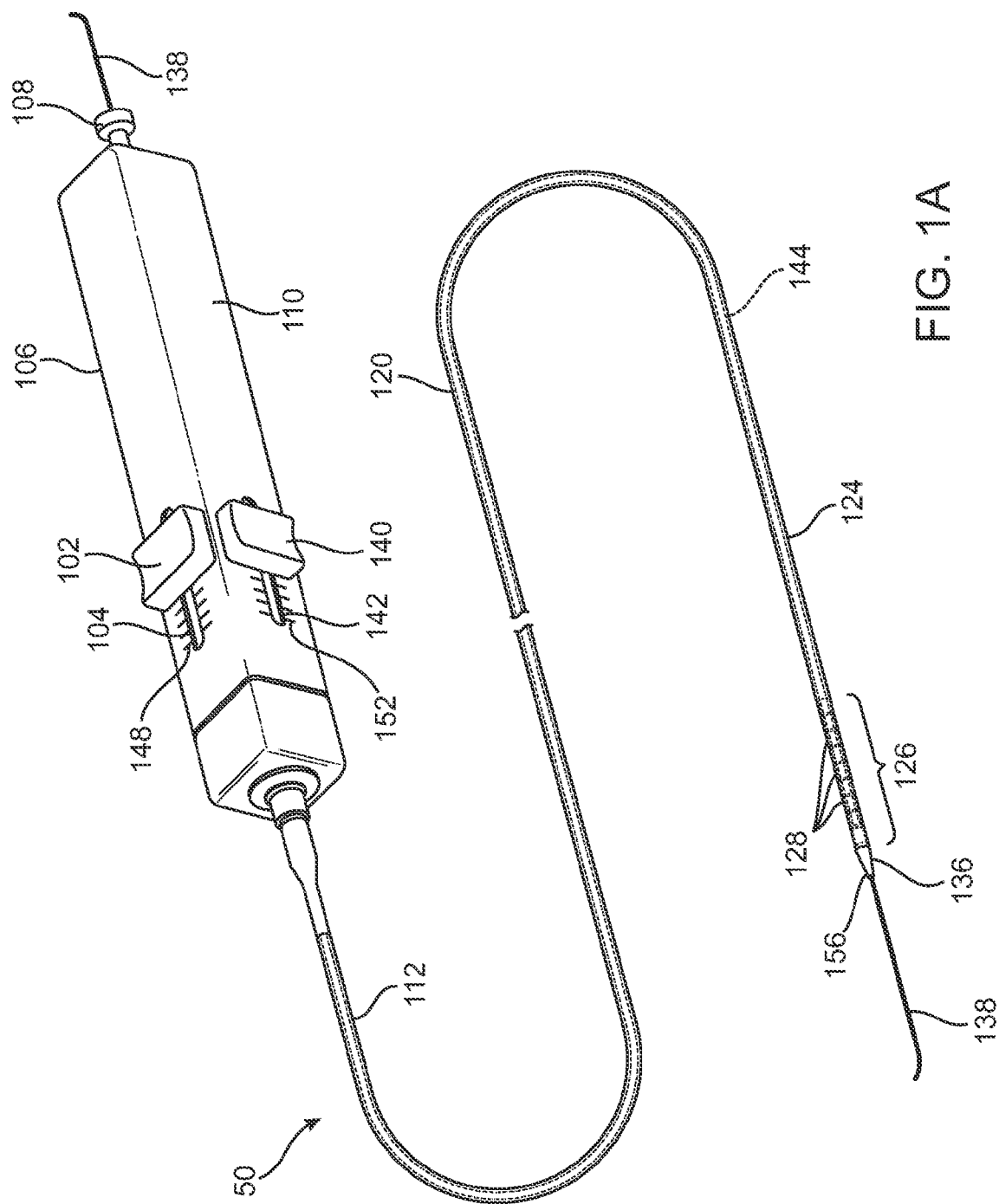
FIG. 1A is a perspective view of an over-the-wire stent delivery catheter in accordance with one embodiment of the present invention.

In the drawings like numerals describe substantially similar components. Referring now to FIG. 1A, a preferred embodiment of an over-the-wire prosthesis delivery catheter 50 comprises a catheter shaft 120 which includes a sheath 124 slidably disposed over a pusher tube 144 which is in turn slidably disposed over an inner shaft 134 (seen in FIG. 1B). A prosthesis 126 is carried near the distal end of the catheter shaft 120 and is covered by sheath 124. Pusher tube 144 is adapted to move past the prosthesis 126 in one direction and to push prosthesis 126 in a second direction and this will be described in greater detail below. A tapered nosecone 136 having a distal exit port 156, composed of a soft elastomeric material to minimize trauma to the vessel during advancement of the delivery catheter 50, is attached to the inner shaft 134 distally of the prosthesis 126. Prosthesis 126 preferably comprises a plurality of self-expanding prostheses 128 mounted under sheath 124 and disposed over inner shaft 134. Sheath 124 covers the self-expanding prostheses 128 and constrains them in a radially contracted configuration until the delivery catheter 50 has been properly positioned at a treatment site. A radiopaque marker 152 (FIG. 1B) near the proximal end of nosecone 136 or optionally a radiopaque marker 151 near the distal end of sheath 124 and a radiopaque marker 153 near the distal end of pusher tube 144 help the operator visualize the delivery catheter under a fluoroscope during a stent procedure. Radiopaque marker 153 also helps the operator to view the distance the pusher 144 has been retracted relative to the radiopaque marker 152 adjacent to nosecone 136. This helps the operator determine how many prostheses 128 to deploy and will be discussed in greater detail below.

As shown in FIG. 1A, handle 106 is attached to a proximal end 112 of the outer sheath 124. The handle 106 performs several functions, including retracting and advancing outer sheath 124 and pusher tube 144 thereby allowing selection and exposure of prosthetic segments 128 so that they may self-expand and be deployed. A guidewire 138 is positioned slidably through adapter 108 of handle 106 and extends through inner lumen 135, exiting distal port 156.

Handle 106 includes a housing 110 which encloses the internal components of the handle 106. Handle 106 allows a physician operator to advance or retract outer sheath 124 and pusher tube 144. The amount of retraction of sheath 124 and pusher tube 144 determine the number of individual prostheses 128 to be deployed thereby establishing the overall length of the prosthesis 126 while ensuring accurate delivery of the individual prostheses 128. The inner shaft 134 is preferably fixed to the handle housing 110, while both outer sheath 124 and pusher tube 144 are coupled to slide mechanisms 102 and 140, respectively. Slide mechanisms 102 and 140 allow both the outer sheath 124 and pusher tube 144 to be retracted and advanced relative to handle 106. Optionally, a single slide mechanism could be used to control motion of the outer sheath 124 and pusher tube 144. Other handle embodiments are described in U.S. patent application Ser. No. 11/614,271, the entire contents of which are hereby incorporated by reference.

The slide mechanism 102 translates along calibrated slot 104. Slide mechanism 102 is coupled with outer sheath 124. Slide mechanism 102 is adapted to retract the outer sheath 124 a selected distance so that the self-expanding tubular prostheses 128 may be exposed for delivery. As sheath 124 is retracted, the distal most section of prosthesis 128 begins to expand. Additional details on the operation of sheath 124 and pusher 144 are described below. The slide mechanism 102 may include optional visual markers 148 that allow an operator to easily determine the length or number of prostheses that have been exposed. In preferred embodiments, slide mechanism 102 may have detents or a ratchet that provides audible or tactile feedback to the operator to facilitate operation of the stent delivery catheter 50 without requiring direct visualization during operation.

Handle 106 also comprises a second control mechanism 140 that translates along calibrated slot 142. Slide mechanism 140 is coupled with the pusher tube 144 and is adapted to retract or advance pusher tube 144 independently of outer sheath 124. Retracting pusher tube 144 allows the number of prostheses 128 to be selected for deployment. Advancement of pusher tube 144 advances the prostheses 128 distally and couples the prostheses 128 together. Slide mechanism 140 may also include optional visual markers 150 that help the physician determine the position of the pusher tube 144 or the number of prostheses 128 selected for deployment or the total length thereof. Additionally, the slide mechanism 140 may comprise detents or a ratchet that further assists physician operation by providing audible or tactile feedback. Further details on operation of the pusher tube 144 and the outer sheath 124 are discussed below.

Handle 106 also permits connection of an external fluid source via adapter 108 attached to the proximal end of handle 106. Fluid may then be injected at the proximal handle end and infused along a lumen in inner shaft 134 into a patient via distal port 156 or other infusion ports (not shown) near the distal end of the delivery catheter 50. The adaptor 108, preferably a Luer connector, is configured to be fluidly coupled with a fluid source such as a syringe or intravenous bag. In alternative embodiments adaptor 108 may be fluidly connected to an inflation lumen 135 in inner shaft 134 which is connected to an optional inflatable balloon (not shown) near the distal end of the catheter 50. An inflation device which may be any commercially available balloon inflation device such as those sold under the trade name "Indeflator™", manufactured by Abbott (formerly Guidant Corporation of Santa Clara, Calif.) may then be connected to adaptor 108 to deliver an inflation fluid to the balloon.

Additional details on materials and construction of other suitable handles and control mechanisms are described in co-pending U.S. patent application Ser. No. 11/148,713, filed Jun. 8, 2005, entitled "Devices and Methods for Operating and Controlling Interventional Apparatus," and co-pending United States Publication No. 2005/0149159, entitled "Devices and Methods for Controlling and Indicating the Length of an Interventional Element," and application Ser. No. 11/614,271, filed Dec. 21, 2006, formerly 021629-003800US), entitled "Custom Length Stent Apparatus," the full disclosures of which are incorporated herein by reference.

Outer sheath 124 may be composed of any of a variety of biocompatible materials, such as but not limited to a polymer like PTFE, FEP, polyimide, Nylon or Pebax, and may be reinforced with a metallic or polymeric braid to resist radial expansion of self-expanding prostheses 128. Similar materials may also be used for the inner shaft 134. Both the inner shaft 134 and outer sheath 124 may also be fabricated from metals such stainless steel or nickel-titanium alloys like nitinol.

Figure 1B:
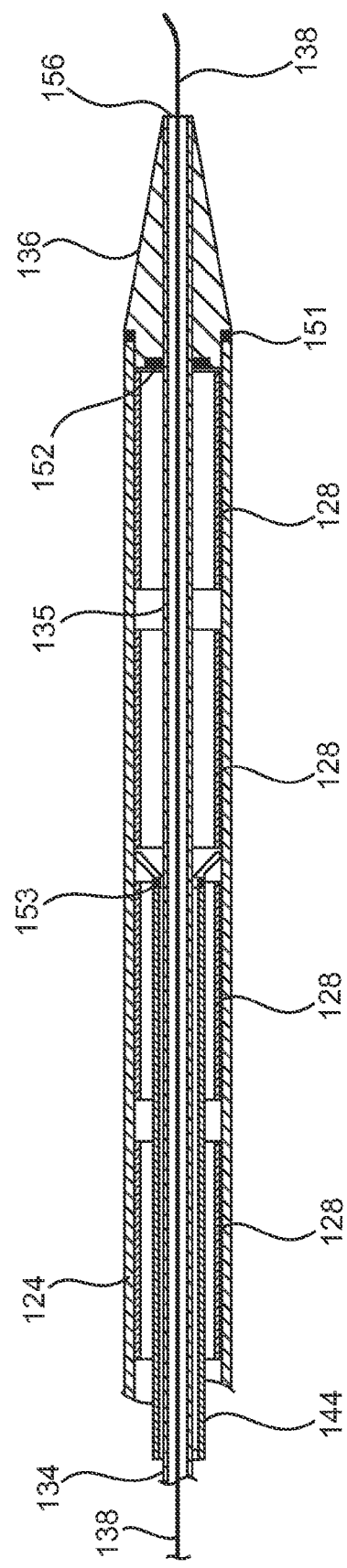
FIG. 1B is a cross section of the distal end of the stent delivery catheter illustrated in FIG. 1A.

Pusher tube 144 is seen in FIG. 1B. Pusher tube 144 is an elongate tube having a central lumen that is slidably disposed over inner shaft 134 and under outer sheath 124. The proximal end of pusher tube 144 is coupled with handle 106 as discussed above. The distal end of pusher 144 is adapted to slide under prostheses 128 when pusher 144 is retracted and to engage a prosthesis 128 and move it distally when pusher 144 is advanced distally. The pusher 144 therefore selects the number of prostheses 128 for delivery and provides enough force to interlock prostheses 128 together as will be discussed below. Pusher tube 144 is often an extruded polymer tube, manufactured from similar materials as the outer sheath 124 or inner shaft 134. The distal tip of pusher 144 typically comprises resilient fingers 166 which may be a polymer or a metal ring with resilient fingers 166 formed from metals such as spring temper stainless steel or nickel-titanium alloy such as nitinol bonded or welded to the distal end of pusher 144. Pusher tube 144 may also be made from nitinol tubing with resilient fingers on the distal end.

Additional aspects of the luminal prosthesis delivery system are described in U.S. patent application Ser. No. 10/306,813, filed Nov. 27, 2002; U.S. patent application Ser. No. 10/637,713, filed Aug. 8, 2003; U.S. patent application Ser. No. 10/738,666, filed Dec. 16, 2003; and U.S. patent application Ser. No. 11/104,305, filed Apr. 11, 2005; the full disclosures of which are hereby incorporated by reference.

Figure 1C:
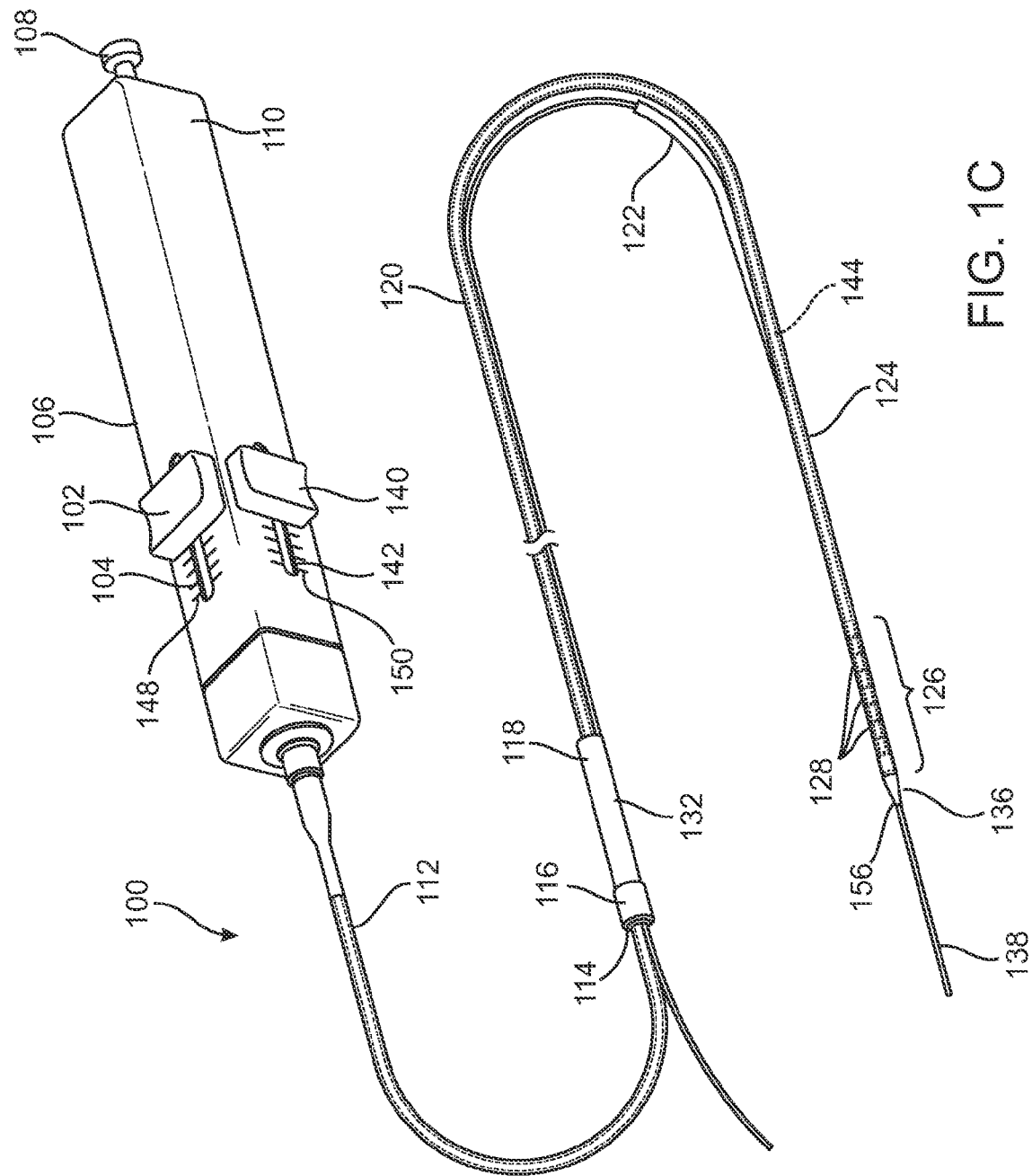
FIG. 1C is a perspective view of a stent delivery catheter in accordance with another embodiment of the present invention.

FIG. 1C illustrates another embodiment of a prosthesis delivery catheter 100 similar to delivery catheter 50 described in FIG. 1A, except that delivery catheter 100 now comprises a guidewire tube and is not a simple over the wire catheter. Delivery catheter 100 comprises a catheter shaft 120 which includes a sheath 124 slidably disposed over a pusher tube 144 which is in turn slidably disposed over an inner shaft 134 (seen in FIG. 2A). A prosthesis 126 is carried near the distal end of the catheter shaft 120 and is covered by sheath 124. Pusher tube 144 is adapted to move past the prosthesis 126 in one direction and to push prosthesis 126 in a second direction as described further below. A tapered nosecone 136 having a distal exit port 156, composed of a soft elastomeric material to minimize trauma to the vessel during advancement of the delivery catheter 50, is attached to the inner shaft 134 distally of the prosthesis 126. Prosthesis 126 preferably comprises a plurality of self-expanding prostheses 128 mounted under sheath 124 and disposed over inner shaft 134. Sheath 124 covers the self-expanding prostheses 128 and constrains them in a radially contracted configuration until the delivery catheter 100 has been properly positioned at a treatment site. A radiopaque marker 152 (FIG. 2A) near the proximal end of nosecone 136 or optionally a radiopaque marker 151 near the distal end of sheath 124 and a radiopaque marker 153 near the distal end of pusher tube 144 help the operator visualize the delivery catheter under a fluoroscope during a stent procedure. Radiopaque marker 153 also helps the operator to view the distance the pusher 144 has been retracted relative to the radiopaque marker 152 adjacent to nosecone 136. This helps the operator determine how many prostheses 128 to deploy and will be discussed in greater detail below.

A guidewire tube 122 is slidably positioned through sheath 124 and inner shaft 134 proximal to the prosthesis 126. A guidewire 138 is positioned slidably through guidewire tube 122 and nosecone 136 and exits a distal exit port 156, extending distally thereof. Additional details on guidewire tube 122 are disclosed in copending U.S. patent application Ser. No. 10/814,581, the entire contents of which are hereby incorporated by reference.

As shown in FIG. 1C, a handle 106 is attached to a proximal end 112 of the outer sheath 124. The handle 106 generally takes the same form as handle 106 which was previously described above with reference to FIG. 1A and controls the movement of outer sheath 124 and pusher tube 144. FIG. 1C shows two sliders 102, 140 used to control sheath 124 and pusher 144, however, optionally, a single slide mechanism could be used to control motion of the outer sheath 124 and pusher tube 144. Other handle embodiments are described in U.S. patent application Ser. No. 11/614,271, the entire contents of which have previously been incorporated by reference. Additional details on materials and construction of other suitable handles and control mechanisms have also been described in co-pending U.S. patent application Ser. No. 11/148,713, filed Jun. 8, 2005, entitled "Devices and Methods for Operating and Controlling Interventional Apparatus," as well as co-pending United States Publication No. 2005/0149159, entitled "Devices and Methods for Controlling and Indicating the Length of an Interventional Element," the full disclosures of which are incorporated herein by reference.

Both outer sheath 124 and guidewire 138 each extend through a slider assembly 132 slidably disposed on the catheter body 120 at a point between its handle 106 and prostheses 128. The slider assembly 132 is adapted for insertion into and sealing with a hemostasis valve, such as on an introducer sheath or guiding catheter, while still allowing relative movement of the outer sheath 124 relative to the slider assembly 132. The slider assembly 132 includes a slider tube 118, a slider body 116, and a slider cap 114.

Outer sheath 124 may be composed of any of a variety of biocompatible materials, such as but not limited to a polymer like PTFE, FEP, polyimide, Nylon or Pebax, and may be reinforced with a metallic or polymeric braid to resist radial expansion of self-expanding prostheses 128. Similar materials may also be used for the inner shaft 134. Both the inner shaft 134 and outer sheath 124 may also be fabricated from metals such as stainless steel or nickel-titanium alloys like nitinol.

Pusher tube 144 is seen in FIG. 2A. Pusher tube 144 generally takes the same form as pusher 144 in FIG. 1B and is an elongate tube having a central lumen that is slidably disposed over inner shaft 134 and under outer sheath 124. The proximal end of pusher tube 144 is coupled with handle 106 as discussed above. The distal end of pusher 144 is adapted to slide under prostheses 128 when pusher 144 is retracted and to engage a prosthesis 128 and move it distally when pusher 144 is advanced distally. The pusher 144 therefore selects the number of prostheses 128 for delivery and provides enough force to interlock prostheses 128 together as will be discussed below. Pusher tube 144 may be fabricated similarly as previously described.

Additional aspects of the luminal prosthesis delivery system are described in U.S. patent application Ser. No. 10/306,813, filed Nov. 27, 2002; U.S. patent application Ser. No. 10/637,713, filed Aug. 8, 2003; U.S. patent application Ser. No. 10/738,666, filed Dec. 16, 2003; and U.S. patent application Ser. No. 11/104,305, filed Apr. 11, 2005; the full disclosures of which are hereby incorporated by reference.

Prosthesis 126 in FIGS. 1A-1C is composed of one or more prostheses 128. Prostheses 128 are disposed over the inner shaft 134 and under sheath 124. Each prosthesis or segment 128 has interlocking tabs on each end and is about 3-50 mm in length, more typically about 10-30 mm in length and preferably being about 15-25 mm in length. Usually 2-20, more typically 2-15 and preferably 5-10 prostheses 128 are positioned axially over the inner shaft 134. Prostheses 128 are preferably positioned with a spacing in between prostheses 128. The spacing is typically between about 0.5 mm and about 1 mm. During selection and deployment of the prostheses 128, the prostheses 128 selected for deployment are pressed together so that interlocking tabs engage and the prostheses 128 are coupled together. Thus, prostheses 128 may be deployed individually or in groups of two or more at a single treatment site within the vessel lumen.

Figure 3A:
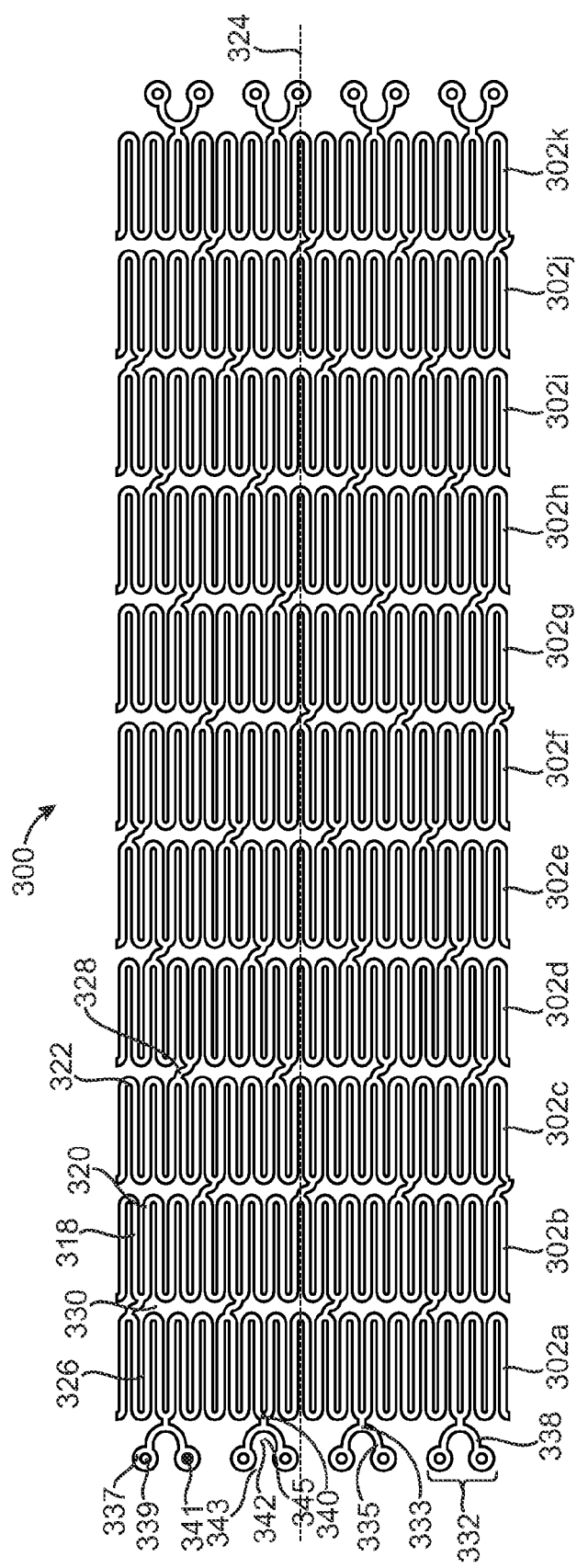
FIG. 3A shows a top view of a prosthesis after it has been unrolled and flattened.

In preferred embodiments the adjacent ends have axially extending members that interleave and engage with one another. In an embodiment seen in FIG. 3A, the geometry of prosthesis 300 is illustrated in an unexpanded configuration, unrolled and flattened out for clarity. In FIG. 3A, prosthesis 300 comprises eleven substantially parallel columns 302a, 302b, 302c, 302d, 302e, 302f, 302g, 302h, 302i, 302j, 302k of open cells 326, spaced apart by a gap 330 and formed around a central axis 324 so that prosthesis 300 has a tubular or cylindrical shape. Each column 302a, 302b, 302c, 302d, 302e, 302f, 302g, 302h, 302i, 302j, 302k is formed from an undulating or sinusoidal or zig-zag or wave pattern 318. The wave pattern 318 is comprised of substantially axial struts 320 joined together by a U-shaped connector 322. The struts 320 are generally parallel to the central axis 324.

In this embodiment, each wave pattern 318 repeats itself sixteen times in each of the eleven parallel columns 302a, 302b, 302c, 302d, 302e, 302f, 302g, 302h, 302i, 302j, 302k of open cells 326, although this number is not intended to be limiting. The number of rows of cells may be increased to provide increased scaffolding of the lumen wall or the number of rows may be decreased to minimize the amount of metal in the prosthesis which contacts the lumen wall. The wave pattern 318 in each column is out-of-phase with the adjacent column, therefore the peak of one wave pattern 318 is adjacent to the trough of a wave 318 pattern in an adjacent column. In addition, the parallel columns 302a, 302b, 302c, 302d, 302e, 302f, 302g, 302h, 302i, 302j, 302k of open cells 326 are joined together by a sigmoidal shaped connector 328 which joins the ends of U-shaped connector 322 together.

The sigmoidal connector 328 generally attaches to the apex of the U-shaped connector 322. Also, the sigmoidal shaped connector 328 attaches generally to every fourth U-shaped connector 322, in each column 302a, 302b, 302c, 302d, 302e, 302f, 302g, 302h, 302i, 302j, 302k, thus there are four sigmoidal shaped connectors 328 between each column 302a, 302b, 302c, 302d, 302e, 302f, 302g, 302h, 302i, 302j, 302k of open cells 326. Additionally, the slope of the sigmoidal shaped connectors 328 generally slopes downward between columns 302a, 302b, 302c, 302d, 302e, 302f, 302g, 302h, 302i, 302j, 302k of open cells 326. For example, the sigmoidal shaped connector 328 between column 302a and 302b is attached to U-shaped connector 322 in column 302a at a point generally at the apex of the U-shaped connector 322 and substantially parallel to the axial struts 320. The sigmoidal connector 328 slopes downward toward the adjacent U-shaped connector 322 in adjacent column 302b and attaches to the adjacent U-shaped connector 322 at a point generally at the apex of U-shaped connector 322 and substantially parallel to the axial struts 320. The sigmoidal shaped connector 322 between columns 302b and 302c similarly joins U-shaped connectors 322, sloping downward. This pattern repeats across the prosthesis 300 so that there are ten sets of sigmoidal shaped connectors 328 with downward slopes. Additionally, sigmoidal shaped connectors 322 are staggered such that across any row of open cells 326, a sigmoidal shaped connector 322 couples columns of open cells 326 every fourth gap 330.

Figure 3B:
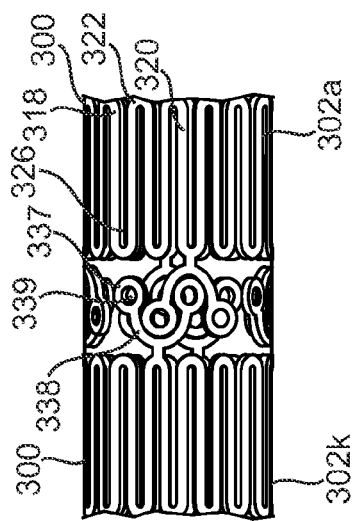
FIG. 3B shows interlocking of two of the prostheses illustrated in FIG. 3A.

Both ends of prosthesis 300 also comprise locking tabs 332 having a narrow neck portion 333 and a wider head portion 335 defined by curved strut 338. Each locking tab 332 is joined to the body of the prosthesis 300 by an axial strut 340 which join to every fourth U-shaped connector 322 at its apex. Strut 338 defines a U-shape or C-shape with enlarged and rounded tips 337 that define a receptacle 339 therein. In some embodiments, the receptacle 339 may be fitted with an optional radiopaque marker 341 to enhance visibility of the prosthesis under a fluoroscope. A space 342 is disposed between ends of locking tabs 332, defined by a narrow inlet portion 343 and a wider receiver portion 345 adapted to receive the rounded tip 337 on a locking tab 332 from an adjacent prosthesis 300. Locking tabs 332 on the opposite end of prosthesis 300 are circumferentially offset with respect to the first end so that adjacent prostheses may interleave and engage with one another. FIG. 3B illustrates how the ends of prostheses 300 with locking tabs 332 engage one another.

Figure 3C:
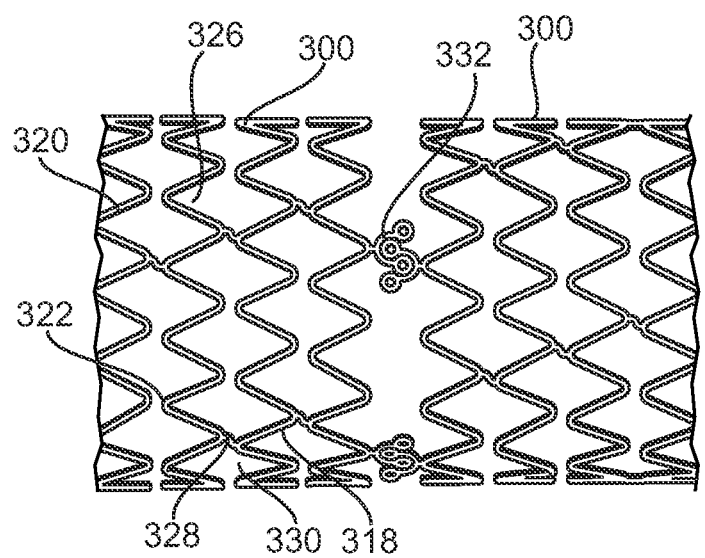
FIG. 3C shows interlocking of two of the prostheses illustrated in FIG. 3A after expansion.
Figure 3D:
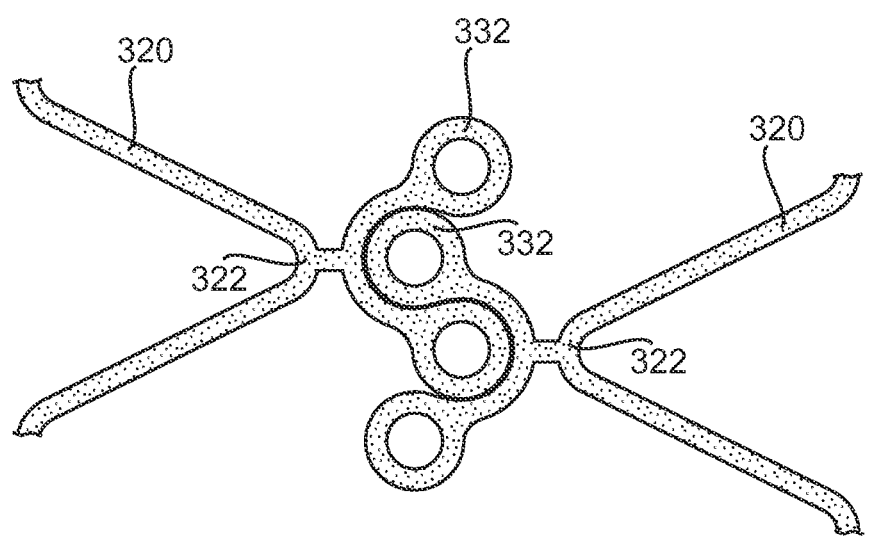
FIG. 3D highlights the interlocking of prostheses shown in FIG. 3C.

FIG. 3C illustrates prosthesis 300 of FIGS. 3A-3B in the expanded configuration and interlocked with an adjacent expanded prosthesis 300. In the expanded configuration, U-shaped connectors 322 deflect outwardly, expanding cells 326. Struts 320, while still substantially straight, are no longer horizontal and thus the period of the sinusoidal-like wave pattern forming each cell 326 has increased and become more angular to form more of a zig-zag, thereby increasing the diameter of the prosthesis. Cells 326 which originally appear as a series of horizontally oriented ovals, now appear as a series of triangles or diamonds. Sigmoidal connectors 328 maintain the spacing 330 between columns of cells 318. Additionally, locking tabs 332 remain coupled between adjacent prostheses 300 even after expansion. FIG. 3D highlights the coupling of locking tabs 332 between adjacent prostheses 300 after expansion.

FIG. 4A illustrates another embodiment of a prosthesis 400 in the unexpanded configuration, unrolled and flattened out for clarity. This embodiment is similar to the embodiment in FIGS. 3A-3D with the major difference being that this embodiment has fewer columns of open cells and different interlocking tabs on either end of the prosthesis.

FIG. 4A shows a preferred embodiment of a prosthesis illustrated in the unexpanded configuration, unrolled and flattened out for clarity. Prosthesis 400 comprises nine substantially parallel columns of 402a, 402b, 402c, 403d, 402e, 402f, 402g, 402h and 402i of open cells 426, spaced apart by a gap 430 and formed around a central axis 424 so that prosthesis 400 has a tubular or cylindrical shape. Each column 402a, 402b, 402c, 403d, 402e, 402f, 402g, 402h and 402i is formed from an undulating or sinusoidal or zig-zag or wave pattern 418. The wave pattern 418 is comprised of substantially axial struts 420 joined together by a U-shaped connector 422. The struts 420 are generally parallel to the central axis 424.

In this embodiment, each wave pattern 418 repeats itself sixteen times in each of the nine parallel columns 402a, 402b, 402c, 403d, 402e, 402f, 402g, 402h and 402i of open cells 426, although this number is not intended to be limiting. The number of rows of cells 426 may be increased to provide increased scaffolding of the lumen wall or the number of rows may be decreased to minimize the amount of metal in the prosthesis which contacts the lumen wall. The wave pattern 418 in each column is out-of-phase with the adjacent column, therefore the peak of one wave pattern 418 is adjacent to the trough of a wave 418 pattern in an adjacent column. In addition, the parallel columns 402a, 402b, 402c, 403d, 402e, 402f, 402g, 402h and 402i of open cells 426 are joined together by a sigmoidal shaped connector 428 which joins the ends of U-shaped connector 422 together.

The sigmoidal connector 428 generally attaches to the apex of the U-shaped connector 422. Also, the sigmoidal shaped connector 428 attaches generally to every fourth U-shaped connector 422, in each column 402a, 402b, 402c, 403d, 402e, 402f, 402g, 402h and 402i, thus there are four sigmoidal shaped connectors 428 between each column 402a, 402b, 402c, 403d, 402e, 402f, 402g, 402h and 402i of open cells 426. Additionally, the slope of the sigmoidal shaped connectors 428 generally slopes downward between columns 402a, 402b, 402c, 403d, 402e, 402f, 402g, 402h and 402i open cells 426. For example, the sigmoidal shaped connector 428 between column 402a and 402b is attached to U-shaped connector 422 in column 402a at a point generally at the apex of the U-shaped connector 422 and substantially parallel to the axial struts 420. The sigmoidal connector 428 slopes downward toward the adjacent U-shaped connector 422 in adjacent column 402b and attaches to the adjacent U-shaped connector 422 at a point generally at the apex of U-shaped connector 422 and substantially parallel to the axial struts 420. The sigmoidal shaped connector 422 between columns 402b and 402c similarly joins U-shaped connectors 422, sloping downward. This pattern repeats across the prosthesis 400 so that there are eight sets of sigmoidal shaped connectors 428 with downward slopes. Additionally, sigmoidal shaped connectors 422 are staggered such that across any row of open cells 426, a sigmoidal shaped connector 422 couples columns of open cells 426 every fourth gap 330.

Both ends of prosthesis 400 comprise interlocking tabs. One end of prosthesis 400 has a locking male tab 432 and the opposite end has a female receiving tab 436. Male tab 432 has a wider head portion 434 defined by arcuate strut 438 unconnected at one end so that it may flex and a narrow neck portion 433 defined by axial strut 436. Axial struts 436 couple the male locking tab 432 to adjacent U-shaped connectors 422 and therefore there also is a spacing 442 between axial struts 436. Female receiving tab 436 also has an enlarged head portion 444 and a narrower neck portion 446. The head portion 444 is formed from arcuate struts 448 shaped like a "C" or a "U," and having bulbous tips 450. The arcuate struts 448 form a receptacle 454 which is adapted to interlock with the enlarged head portion 434 of male locking tab 432. The neck portion is formed from a wide strut 452 which joins with adjacent axial struts 420, replacing the U-shaped connector 422. Female tabs 436 are staggered relative to male tabs 432 so that adjacent prostheses may interlock with each other. FIG. 4B illustrates how the ends of prostheses 400 with tabs 432 and 436 engage one another.

Figure 5A:
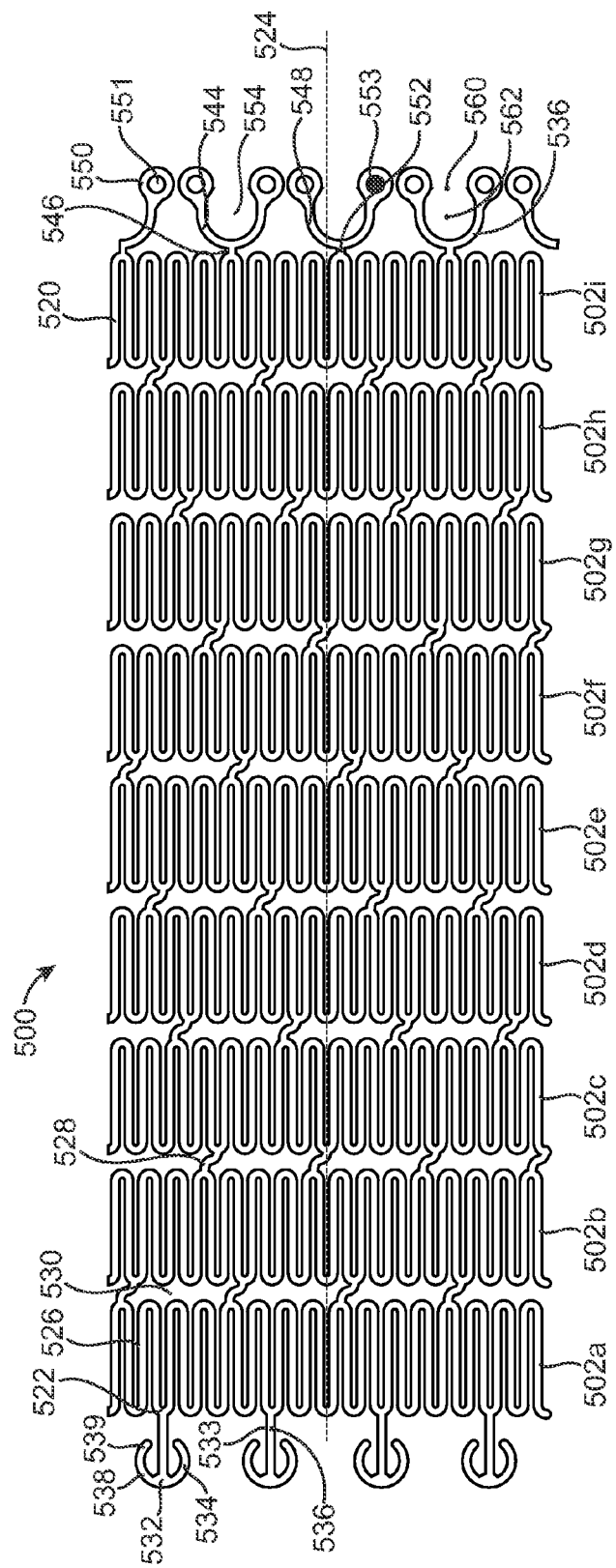
FIG. 5A shows a top view of still another embodiment of a prosthesis after it has been unrolled and flattened.

FIG. 5A shows another embodiment of an interlocking prosthesis 500 in the unexpanded configuration, unrolled and flattened out for clarity. This embodiment is similar to that shown in FIGS. 4A-4B with the major difference being the interlocking tabs on either end of the prosthesis 500. The overall geometry of prosthesis 500 is the same as prosthesis 400 above. For example, prosthesis 500 also has nine substantially parallel columns 502a, 502b, 502c, 502d, 502e, 502*f*, 502*g*, 502*h* and 502*i* of open cells 526 spaced apart by a gap 530 and formed around a central axis 524 so that prosthesis 500 has a tubular or cylindrical shape. Each column 502*a*, 502*b*, 502*c*, 502*d*, 502*e*, 502*f*, 502*g*, 502*h* and 502*i* has the same undulating wave pattern 418 as prosthesis 400 with a sigmoidal connector 528 coupling the nine columns 502*a*, 502*b*, 502*c*, 502*d*, 502*e*, 502*f*, 502*g*, 502*h* and 502*i* together. Other aspects of the sigmoidal connector 528 are generally the same as sigmoidal connector 428 described above with respect to FIGS. 4A-4B.

Both ends of prosthesis 500 comprise interlocking tabs. One end of prosthesis 500 has a locking male tab 532 and the opposite end has a female receiving tab 536. Male tab 532 has a wider head portion 534 defined by an arcuate strut 538 forming a "C" shape and having free ends 539 that may flex, and a narrow neck portion 533 defined by an axial strut 536. The axial strut 536 is coupled with the C-shaped arcuate strut 538 approximately at the center of the concave portion of the "C." The axial strut 536 couples the male locking tab 532 to the prosthesis 500 at the apex of U-shaped connector 522 in open cell 526. There are four male locking tabs 532 on one end of prosthesis 500, spaced apart every four rows of open cells 526.

Figure 5B:
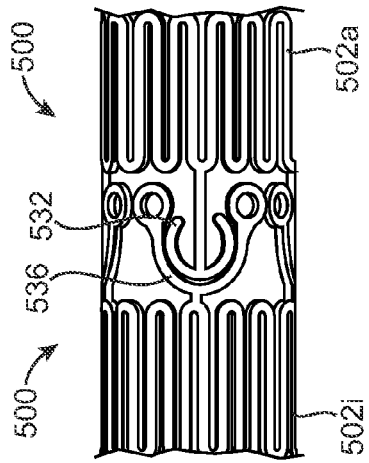
FIG. 5B shows interlocking of two of the prostheses illustrated in FIG. 5A.

The opposite end of prosthesis 500 has a female receiving tab 536 which includes an enlarged head portion 544 and a narrower neck portion 546. The head portion 544 is formed from an arcuate strut 548 shaped like a "C" or a "U," and having enlarged tips 550 defining a receptacle 551 therein. An optional radiopaque marker 553 may be press-fit, welded or bonded into receptacle 551. Radiopaque markers are commonly fabricated from gold, platinum, iridium or tantalum. The arcuate strut 548 forms another receptacle 554 having a narrow inlet portion 560 and a wider receiver portion 562 which is adapted to interlock with the enlarged head portion 534 of male locking tab 532. The neck portion 546 is formed from a strut 552 which joins with the adjacent axial struts 520 which form open cells 526. Strut 552 joins with strut 520 at the apex of U-shaped connector 522. Female receiving tabs 536 are staggered with respect to male tabs 532 so that adjacent prostheses 500 may interlock with each other. Prostheses 500 interlock with one another by pressing them together. FIG. 5B illustrates how the ends of prostheses 500 with tabs 532 and 536 engage one another.

Other interleaving stent embodiments are described in copending U.S. patent application Ser. No. 10/738,666 filed Dec. 16, 2003; U.S. patent application Ser. No. 10/957,079 filed Sep. 30, 2004; and U.S. Provisional Application No. 60/784,309 filed Mar. 20, 2006, the entire contents of which are incorporated herein by reference.

Prostheses 128 are preferably composed of an elastic or superelastic shape memory alloy such as Nitinol so that the prostheses 128 resiliently self-expand upon release into a vessel by retraction of the sheath 124. Other possible materials include a spring temper metal such as stainless steel, cobalt-chromium or ELGILOY™ so the prostheses 128 may self-expand in the body lumen at the target treatment site. In the case of self-expanding prostheses 128, an inflation balloon is not required but may still be used for predilation of a lesion or augmenting expansion of the self-expanding stent segments 128 (e.g. postdilation or tacking). Other materials such as biocompatible polymers may be used to fabricate prosthetic stent segments that self-expand, and these materials may further include bioabsorbable or bioerodable properties.

In other embodiments, prostheses 128 may have any of a variety of common constructions, such as but not limited to those described in U.S. patent application Ser. No. 10/738, 666 filed Dec. 16, 2003, which was previously incorporated by reference. Constructions may include for example, closed cell constructions including expansible ovals, ellipses, box structures, expandable diamond structures, etc. In addition, the closed cells may have complex slotted geometries such as H-shaped slots, I-shaped slots, J-shaped slots, etc. Suitable open cell structures include zig-zag structures, serpentine structures, and the like. Such conventional stent structures are well described in the patent and medical literature. Specific examples of suitable stent structures are described in the following U.S. patents, the full disclosures of which are incorporated herein by reference: U.S. Pat. Nos. 6,315,794; 5,980, 552; 5,836,964; 5,527,354; 5,421,955; 4,886,062; and 4,776, 337.

In preferred embodiments, prosthetic stent segments 128 may be coated, impregnated, infused or otherwise coupled with one or more drugs that inhibit restenosis, such as Rapamycin, Everolimus, Biolimus A9, Paclitaxel, analogs, pro-drugs, or derivatives of the aforementioned, or other suitable agents, preferably carried in a durable or bioerodable carrier of polymeric or other suitable material. Alternatively, stent segments 128 may be coated with other types of drugs or therapeutic materials such as antibiotics, thrombolytics, anti-thrombotics, anti-inflammatories, cytotoxic agents, anti-proliferative agents, vasodilators, gene therapy agents, radioactive agents, immunosuppressants, chemotherapeutics, endothelial cell attractors or promoters and/or stem cells. Such materials may be coated over all or a portion of the surface of stent segments 128, or stent segments 128 may have a porous structure or include apertures, holes, channels, or other features in which such materials may be deposited.

Referring now to FIGS. 2A-2E, the deployment of selected prostheses to treat a lesion is shown in accordance with an exemplary embodiment. While the embodiment will be described in the context of a femoral artery stent procedure, it should be understood that the invention may be employed in any variety of coronary or peripheral arteries, blood vessels and other body lumens in which stents or tubular prostheses are deployed, including the carotid and iliac arteries, other arteries or veins, as well as non-vascular body lumens such as the ureter, urethra, fallopian tubes, the hepatic and biliary duct and the like. The delivery catheter is introduced into a treatment vessel first, by placing an introducer sheath (not illustrated) into the target peripheral artery, typically using a percutaneous procedure such as the Seldinger technique or by surgical cutdown. In this exemplary embodiment, the target vessel is a femoral artery. The introducer sheath is then advanced slightly into the femoral artery. A guidewire 138 is then inserted through the introducer and advanced into the target vessel V where a lesion L to be treated is located. The proximal end of guidewire 138 is then inserted through distal port 156 of nosecone 138 and through inner lumen 135 of inner shaft 134, exiting handle 106 at adapter 108 which is outside the patient's body. Optionally, a guide catheter may also be employed.

FIG. 2A shows a stent delivery catheter 200 slidably advanced over the guidewire 138 into the vessel V so that nosecone 138 is distal to lesion L. Self-expanding tubular prostheses 128 having ends spaced apart are disposed over inner shaft 134 and constrained by outer sheath 124. In this embodiment, four prostheses 128 are carried by the stent delivery catheter 200, although this is not intended to be limiting. The number of prostheses may be varied to accommodate different lesion lengths.

Outer sheath 124 has a high hoop strength near the distal end such that the outer sheath 124 is able to prevent the self-expanding prostheses 128 from expanding when the outer sheath 124 is disposed thereover. This may be accomplished by using an outer sheath 124 with a suitable wall thickness or the sheath 124 may also have a distal portion formed from a metal or polymer reinforced with a metallic or polymeric braid to resist radial expansion of the self-expanding prostheses 128.

In this embodiment, each prosthesis 128 has a length approximately 20 mm long. Thus the delivery catheter 200 is adapted to deliver a prosthesis having a total length from about 20 mm long, up to 80 mm long, in 20 mm increments. Other lengths and quantities of prostheses 128 may be employed and this exemplary embodiment is not meant to limit the scope of the present invention.

Figure 2C:
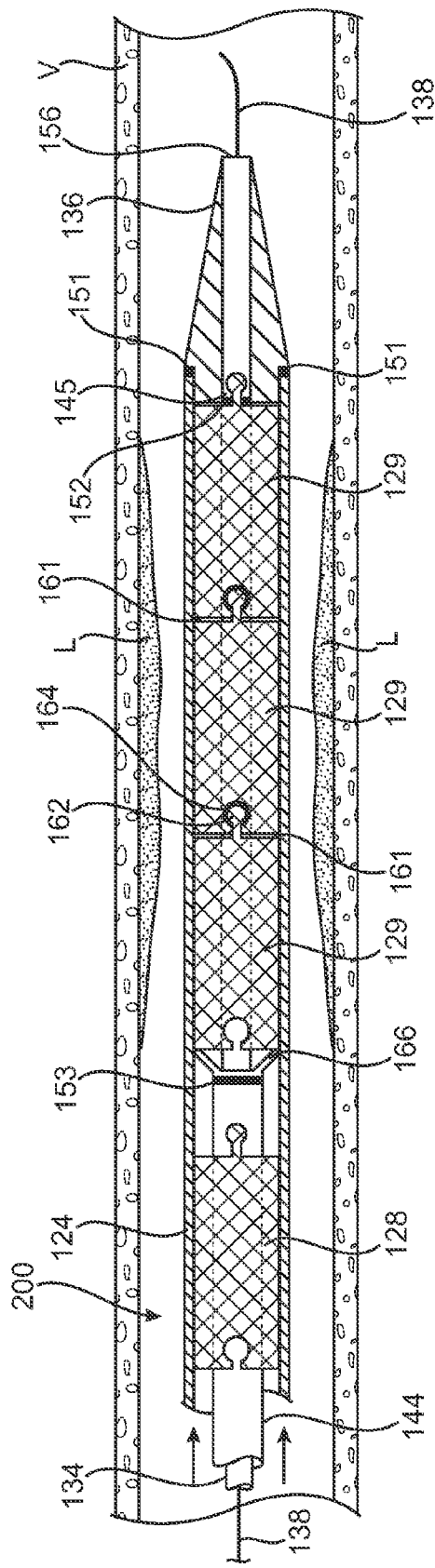

Radiopaque marker 152 is disposed near the proximal end of nosecone 138 or alternatively, radiopaque marker 152 may be disposed on inner shaft 134 near the proximal end of nosecone 138. Radiopaque marker 153 is disposed near the distal end of pusher 144. Radiopaque markers are typically fabricated from gold, platinum, iridium or tantalum and are well known in the art. Radiopaque markers 152 and 153 help an operator to visualize the tip of delivery catheter 200 under fluoroscopy as well as determining the number of prostheses 128 to deploy to traverse the lesion L. In some embodiments, an optional radiopaque marker 151 may be disposed near the distal end of outer sheath 124 so that sheath position may also be observed under fluoroscopy. Pusher tube 144 is also seen in FIG. 2A disposed over inner shaft 134. The distal end pusher tube 144 comprise several resilient fingers 166 which radially extend outward such that pusher tube 144 may be retracted proximally past prostheses 128 but when pusher 144 is advanced distally, the resilient fingers 166 engage a prosthesis 128 so that the prosthesis 128 is advanced distally as the pusher 144 is advanced. Distal motion of prosthesis 128 allows adjacent prostheses 128 having interlocking tabs 162 to engage with receptacle 164, eliminating gap 160. Pusher tube 144 also serves as a backstop to prevent proximal motion of prostheses 128. Additional details on these elements will be discussed in greater detail below, with respect to FIGS. 2B-2E.

Referring now to FIG. 2B, the lesion L to be treated is typically visualized by introducing contrast media into the target vessel V and observing the resulting image under a fluoroscope. Radiopaque markers 152, 153 and optional radiopaque marker 151 are used to help visualized the position of the delivery catheter 200 relative to the lesion L as well as to visualize the length of prostheses 129 selected for deployment relative to the target lesion L. Radiopaque marker 152 is typically disposed near the proximal end of nosecone 136 but in alternative embodiments marker 152 may also be disposed on the inner shaft 134 near the proximal end of nosecone 136. Delivery catheter 200 is advanced until radiopaque marker 152 is near the distal edge of lesion L. Pusher 144 will later be retracted proximally until it is near the proximal end of lesion L. The lesion therefore traverses the region between radiopaque markers 152 and 153. An optional radiopaque marker 151 disposed near the distal end of outer sheath 124 allows the user to observed sheath position during the stenting procedure.

In FIG. 2B, pusher tube 144 is retracted proximally until radiopaque marker 153 is near the proximal edge of lesion L. The distal end 166 pusher tube 144 comprises a plurality of resilient, radially extending inclined fingers 166, thus pusher tube 144 may be retracted proximally under prostheses 128 without displacing them. Retracting pusher 144 selects the number of prostheses 129 to be deployed and that will provide a total prosthesis 126 length that traverses the length of lesion L. Pusher 144 tube extends to the proximal end of delivery catheter 200 and retraction of pusher tube 144 is accomplished using a control mechanism such as slider 140 in FIG. 1A or 1C.

In FIG. 2C, prostheses 129 are advanced distally until they engage and interlock with one another. Pusher tube 144 is advanced distally until it engages the proximal-most end of the proximal prosthesis 129 selected for delivery. The distal end of pusher tube 144 has resilient and radially extending inclined fingers 166. Advancing pusher tube 144 distally causes the fingers 166 to engage with the proximal-most prosthesis 129 selected for delivery. Further advancement of pusher tube 144 advances the selected prostheses 129 until the distal-most prosthesis 129 of those selected butts up against the proximal end of nose cone 136. Nosecone 136 has a recessed region 145 in which interlocking tab 162 may be received so that the distal-most prosthesis 129 can fit flush against nosecone 136. As pusher tube 144 is advanced, prostheses 129 selected for deployment bunch up together until locking tabs 162 engage and interlock with receivers 164 on an adjacent prosthesis 129. The gap 160 that existed between prostheses 128 prior to deployment therefore is reduced significantly to a slight gap or no gap 161 as prosthesis 129 ends are engaged with one another during deployment. Additionally, if after pushing prostheses 129 together, a longer total length is required, the steps illustrated in FIGS. 2B-2C may be repeated in order to create a longer "stent train."

Figure 2D:
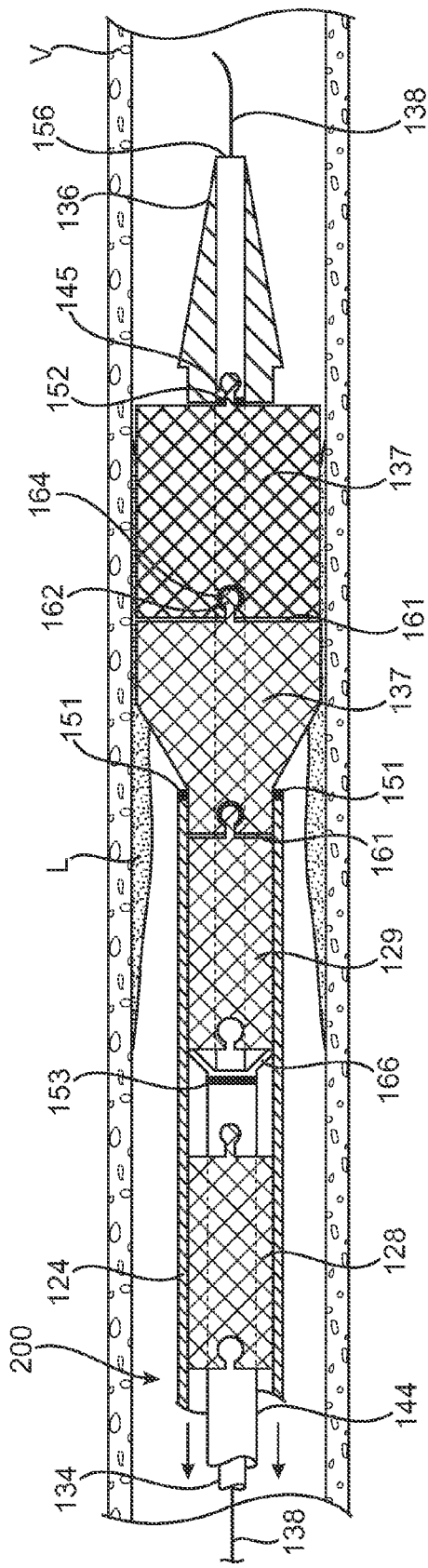

In FIG. 2D, the constraint covering prostheses 129 selected for deployment is removed. In FIG. 2D, outer sheath 124 is retracted proximally. Retraction of outer sheath 124 is accomplished using a control mechanism such as slider 102 in FIG. 1A or 1C. Retracting outer sheath 124 removes the constraint and exposes prostheses 129, allowing them to self-expand into lesion L. As outer sheath 124 is retracted, the exposed portion of prostheses 129 self-expand to a final shape 137 matching lesion L. Prosthesis 129 is prevented from jumping or "watermelon seeding" away from delivery catheter 200 because the prosthesis 129 being deployed is interlocked with an adjacent prosthesis 129 maintained in the delivery catheter 200 and constrained by outer sheath 124. The position of the outer sheath 124 may be monitored by the operator by visualizing an optional radiopaque marker 151 on the distal end of outer sheath 124, or the operator may determine sheath position by observing the position of slider 102. Pusher tube 144 also serves as a backstop to prevent proximal displacement of prostheses 129 that might occur as a result of outer sheath 124 passing distally thereover.

Figure 2E:
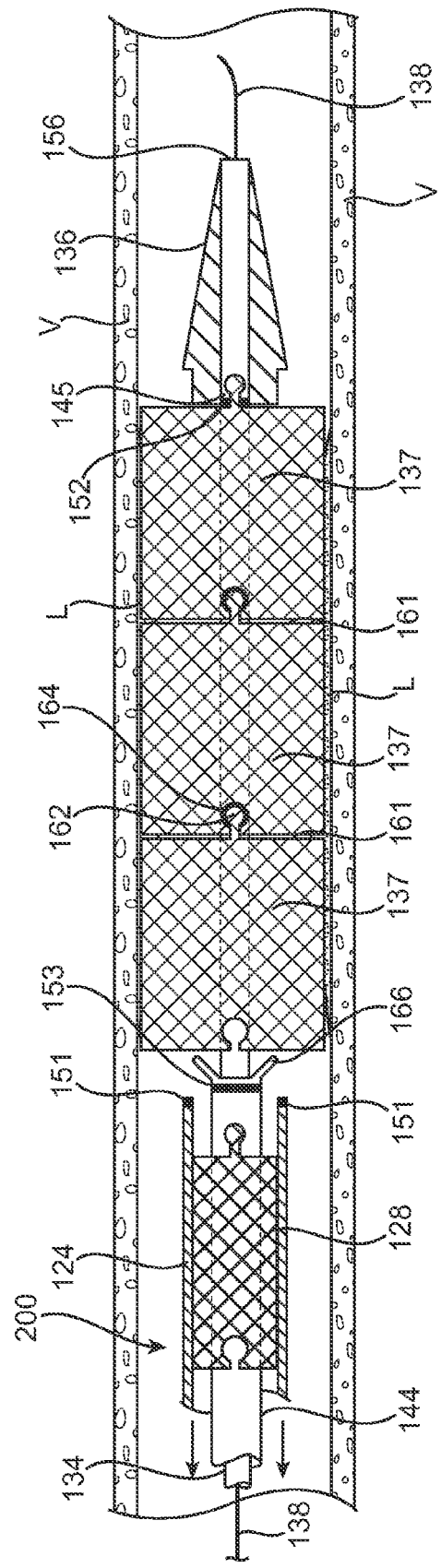

In FIG. 2E, outer sheath 124 is retracted proximally until all prostheses 129 selected for deployment are unconstrained and they self-expand into the lesion L. If an additional prosthesis 128 is required to treat the lesion L, the pusher tube 144 may be retracted proximally so as to select an additional prosthesis 128 and it may be deployed in similar manner to that previously described. Once all prostheses 129 have been deployed, outer sheath 124 may be advanced distally until it engages nosecone 136 and the entire delivery catheter 200 may be removed from the treatment site. Alternatively, inner shaft 134 may be retracted into outer sheath 124 until nosecone 136 engages outer sheath 124 and then the entire delivery catheter 200 may be withdrawn.

While the exemplary embodiments have been described in some detail for clarity of understanding and by way of example, a variety of additional modifications, adaptations and changes may be clear to those of skill in the art. Hence, the scope of the present invention is limited solely by the appended claims.

What is claimed is:

1. A method for delivering a prosthesis to a body lumen, the method comprising:
   introducing into the body lumen one or more self-expanding tubular prostheses carried at axially spaced apart locations along an elongate flexible member, the self-expanding tubular prostheses being axially separated and unlocked within a sheath and constrained in a contracted configuration within the sheath, the body lumen having a lesion with a lesion length;
   selecting a first group of the self-expanding tubular prostheses for delivery by proximally retracting a pusher member disposed proximal of the first group of prostheses, the first group of prostheses having a combined length that substantially traverses the lesion length;
   distally advancing the pusher member to axially translate the selected first group of prostheses within the sheath to bring the first group of prostheses into locking engagement with each other within the sheath; and
   uncovering the first group of prostheses from the sheath so that they are unconstrained from expansion, wherein the first group expands at the first treatment site.

2. The method of claim 1, wherein the first group expands at the first treatment site while at least a second group of prostheses is retained within the sheath.

3. The method of claim 1, further comprising:
   selecting one or more additional self-expanding tubular prostheses; and
   bringing the additional self-expanding tubular prostheses into engagement with the first group within the sheath so that the additional prostheses interlock with the first group.

4. The method of claim 1, wherein the pusher member has a flexible engagement member that is deflected by the prostheses as the pusher member is retracted proximally.

5. The method of claim 4, wherein the flexible engagement member comprises a plurality of resilient fingers.

6. The method of claim 5, wherein each of the plurality of resilient fingers extend radially away from the pusher member, and wherein one or more of the plurality of resilient fingers engages a proximal-most prosthesis of the first group when advanced distally to bring the first group into engagement with each other.

7. The method of claim 1, wherein axially translating the at least one prosthesis comprises engaging the prosthesis with a flexible engagement member disposed on the pusher member.

8. The method of claim 1, further comprising stopping the first group of prostheses from moving distally with a stopping element disposed on the elongate flexible member.

9. The method of claim 1, wherein uncovering the first group comprises proximally retracting the sheath.

10. The method of claim 1, further comprising releasing a therapeutic agent from the first group after expansion at the treatment site.

11. The method of claim 10, wherein the therapeutic agent comprises an anti-restenosis agent.

12. The method of claim 1, wherein the plurality of self-expanding tubular prostheses have a length in the range of about 5 mm to about 50 mm.

13. The method of claim 1, wherein each of the plurality of self-expanding tubular prostheses has the same length.

14. The method of claim 1, wherein at least one of the plurality of self-expanding tubular prostheses has a different length than at least another of the prostheses.

15. The method of claim 1, wherein the prosthesis comprises a plurality of substantially parallel columns of open cells, the columns spaced apart and formed from a zig-zag pattern of substantially axial struts joined together with a connector.

16. The method of claim 15, wherein the connector comprises a U-shaped portion.

17. The method of claim 15, wherein the open cells in a first column are out of phase with the open cells in an adjacent column.

18. The method of claim 1, wherein a plurality of bridges join the columns of open cells together.

19. The method of claim 18, wherein the bridges are sigmoidally shaped.

20. The method of claim 1, wherein a prosthesis comprises an interlocking tab disposed on a first end of the prosthesis and adapted to interlock with an adjacent prosthesis.

21. The method of claim 20, wherein the prosthesis comprises a mating tab disposed on a second end of the prosthesis opposite the first end, the mating tab adapted to interlock with an interlocking tab on an adjacent prosthesis.

22. The method of claim 20, wherein the interlocking tab comprises one or more struts defining an aperture therein.

23. The method of claim 20, wherein the interlocking tab comprises a radiopaque marker.

24. The method of claim 1, wherein the interlocked prostheses prevent the prostheses from jumping away from the elongate flexible member when the first group is unconstrained.

25. The method of claim 1, wherein each of the prostheses comprises a distal U-shaped interlocking member and a proximal U-shaped interlocking member, and wherein the first group of prostheses are interlocked by mating distal U-shaped interlocking members and proximal U-shaped interlocking members of adjacent prostheses.

26. The method of claim 1, wherein the elongate flexible member comprises a radiopaque marker at a distal end of the elongate flexible member, and wherein the pusher member disposed within the elongate flexible member comprises a radiopaque marker at a distal end of the pusher member, the method further comprising:
   retracting the pusher member proximally to select the first group of prostheses; and
   bringing the first group of prostheses into engagement with each other by advancing the pusher member distally, wherein the radiopaque marker at the distal end of the elongate flexible member and the radiopaque marker at the distal end of the pusher member facilitate in selecting the first group of prostheses so that the combined length of the first group substantially traverses the lesion length.

* * * * *